(12) United States Patent
Papahadjopoulos et al.

(10) Patent No.: US 6,426,086 B1
(45) Date of Patent: Jul. 30, 2002

(54) PH-SENSITIVE, SERUM-STABLE LIPOSOMES

(75) Inventors: Demetrios Papahadjopoulos, deceased, late of San Francisco, CA (US), by executor Francis Szoka; Olivier Meyer, Strasbourg (FR); Jean-Christophe Leroux, Montreal (CA)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/243,098

(22) Filed: Feb. 2, 1999

Related U.S. Application Data
(60) Provisional application No. 60/073,471, filed on Feb. 3, 1998.

(51) Int. Cl.$^7$ .............................................. A61K 9/127
(52) U.S. Cl. ................... 424/450; 424/1.21; 424/9.321; 424/9.51; 424/94.3; 428/402.2; 935/54
(58) Field of Search ............................... 424/450, 1.21, 424/9.321, 9.51, 417, 94.3, 812; 436/829; 935/54; 428/402.2

(56) References Cited

U.S. PATENT DOCUMENTS
4,448,765 A * 5/1984 Ash ............................. 424/450
5,891,468 A * 4/1999 Martin ......................... 424/450

OTHER PUBLICATIONS

Alving et al., "Liposomes Containing Liquid A: A Potent Nontoxic Adjuvant for a Human Malaria Sporozoite Vaccine," *Immunology Letters*, 24:275–280 (1990).

Brazel et al., "Pulsatile Local Delivery of Thrombolytic and Antithrombotic Agents Using Poly(N–isopropylacrylamide –co–methacrylic acid) Hydrogels," *J. Controlled Release*, 39:57–64 (1996).

Chen et al., "Graft Copolymers that Exhibit Temperature –induced Phase Transitions Over a Wide Range of pH," *Nature*, 373:49–52 (1995).

Collins et al., "Structural and Functional Comparisons of pH–Sensitive Liposomes composed of Phosphatidylethanolamine and Three Different Diacylsuccinylglycerols," *Biochimica et Biophysica Acta*, 1025:234–242 (1990).

Chung et al., "pH–Sensitive, Cation–Selective Channels Formed by a Simple Synthetic Polyelectrolyte in Artificial Bilayer Membranes," *Macromolecules*, 29:4636–4641 (1996).

*Liposomes as Tools in Basic Research and Industry*, eds. Philippot and Schuber, CRC Press, Boca Raton, Fl. pp. 177–188 (1995).

*Liposomes as Tools in Basic Research and Industry*, eds. Philippot and Schuber, CRC Press, Boca Raton, Fl. pp. 201–214 (1995).

(List continued on next page.)

Primary Examiner—Gollamudi S. Kishore
(74) Attorney, Agent, or Firm—Townsend and Townsend and Crew, LLP

(57) ABSTRACT

This invention relates to the field of liposomes. In particular, this invention provides novel liposomes that are pH-sensitive, yet are also stable in serum. The liposomes are complexed with a molecule comprising a thermally-sensitive polymer showing lower critical solution temperature behavior in aqueous solutions, said thermally-sensitive polymer bearing a hydrophobic substituent and a pH sensitive substituent, wherein said hydrophobic substituent is less than 10 kD and which pH sensitive substituent remains ionizable following said covalent bonding to said thermally-sensitive polymer, and whose pH sensitive does not depend on cleavage of the covalent bond to said thermally-sensitive polymer. The invention further relates to methods of conferring pH sensitivity upon liposomes by complexing the liposomes with such molecules.

33 Claims, 3 Drawing Sheets

OTHER PUBLICATIONS

Connor et al., "Biodistribution of pH–Sensitive Immunoliposomes," *Biochimica et Biophysica Acta*, 884:474–481 (1986).

Dong et al., "A Novel Approach for Preparation of ph–Sensitive Hydrogels for Enteric Drug Delivery," *J. Controlled Release*, 15:141–152 (1991).

Ellens et al., "pH–Induced Destabilization of Phosphatidylethanolamine–Containing Liposomes: Role of Bilayer Contact," *Biochemistry*, 23:1532–1538 (1984).

Feil et al., "Effect of Comonomer Hydrophilicity and Ionization on the Lower Critical Solution Temperature of N–Isopropylacrylamide Copolymers," *Macromolecules*, 26:2496–2500 (1993).

Franzin et al., "Destabilization of Cationic Liquid Vesicles by an Anionic Hydrophobically Modified Poly(N–Isopropylacrylamide) Copolymer: A Solid–State $^{31}P$ NMR and $^2H$ NMR Study," *Biochimica et Biophysica Acta*, 1415:219–234 (1998).

Hayashi et al., "Temperature–Controlled Release Property of Phospholipid Vesicles Bearing a Thermo–Sensitive Polymer," *Biochimica et Biophysica Acta*, 1280:127–134 (1996).

Hayashi et al, "Temperature–Dependent Associating Property of Liposomes Modified with a Thermosensitive Polymer," *Bioconjugate Chem.*, 9:382–389 (1998).

Hirotsu et al., "Volume–phase Transitions of Ionized N–Isopropylacrylamide Gels," *J. Chem. Phys.*, 87(2):1392–1395 (1987).

Kim et al., "Temperature–Sensitivity of Liposomal Lipid Bilayers Mixed with Poly (N–Isopropylacrylamide –co–acrylic Acid)," *J. Biochem.*, 121:15–19 (1997).

Kim et al., "pH/Temperature–Sensitive Polymers for Macromolecular Drug Loading and Release," *J. Controlled Release*, 28:143–152 (1994).

Kim et al., "Temperature–Sensitive Releases From Liposomes Containing Hydrophobically Modified Poly(N–Isopropylacrylamide," *Korean J. Chem. Eng.*, 16:28–33 (1999).

Kirpotin et al., "Liposomes with Detachable Polymer Coating: Destabilization and Fusion of Dioleoylphosphatidylethanolamine Vesicles Triggered by Cleavage of Surface–Grafted Poly(Ethylen Glycol)," *FEBS Letters*, 388:115–118 (1996).

Kono et al., "Novel pH–Sensitive Liposomes: Liposomes Bearing a Poly(Ethylen Glycol) Derivative with Carboxyl Group," *Biochimica et Biophysica Acta*, 1193:1–9 (1994).

Kono et al., "Temperature–Sensitive Liposomes: Liposomes Bearing Poly(N–Isopropylacrylamide)," *J. Controlled Release*, 30:69–75 (1994).

Kono et al., "Thermosensitive Polymer–Modified Liposomes Combining Protonatable Double–Chain Amphiphiles with Phosphatidylethanolamine," *Biochemistry*, 26:3267–3276 (1987).

Litzinger et al., "Phosphatidylethanolamine Liposomes: Drug Delivery, Gene Transfer and Immunodiagnostic Applications," *Biochimica et Biophysica Acta*, 1113:201–227 (1992).

Liu et al., "Small, but Not Large, Unilamellar Liposomes Composed of Dioleoylphosphatidylethanolamine and Oleic Acid Can Be Stabilized by Human Plasma," *Biochemistry*, 28:7700–7707 (1989).

Liu et al., "pH–Sensitive Plasma–Stable Liposomes with Relatively Prolonged Residence in Circulation," *Biochimica et Biophysica Acta*, 1022:348–354 (1990).

Murthy, N., et al. "Design of Polymer to Increase the Efficiency of Endosomal Release of Drugs," *Proc. Intern. Symp. Control Rel. Bioact. Mater.*, 25:224–225 (1998).

Polozova et al., "Effect of Polymer Architecture on the Interactions of Hydrophobically–Modified Poly–(N–Isopropylamides) and Liposomes," *Colloids and Surfaces A Physicochemcial and Engineering Aspects*, 147:17–25 (1999).

Polozova et al., "Mechanism of the Interaction of Hydrophobically–Modified Poly–(N–Isopropylacrylamides) with Liposomes," *Biochimica et Biophysica Acta*, 1326:213–224 (1997).

Ringsdorf et al., "Interaction of Hydrophobically–Modified Poly–N–Isopropylacrylamides with Model Membranes—or Playing a Molecular Accordion," *Angew. Chem. Int. Ed. Engl.*, 30:315–318 (1991).

Ringsdorf et al., "Interactions of Liposomes and Hydrophobically–Modified Poly–(N–Isopropylacrylamides): An Attempt to Model the Cytoskeleton," *Biochimica et Biophysica Acta*, 1153:335–344 (1993).

Slepushkin et al., "Sterically Stabilized pH–Sensitive Liposomes," *J. Biological Chemistry*, 272(4):2382–2388 (1997).

Straubinger et al., "pH–Sensitive Liposomes Mediate Cytoplasmic Delivery of Encapsulated Macromolecules," *FEBS Letters*, 179(1):148–154 (1985).

Tirrell et al., "pH Sensitization of Phospholipid Vesicles Via Complexation with Synthetic Poly(carboxylic Acid)," *Annals New York Academy of Sciences*, 446:237–248 (1985).

Wagner et al., "Influenza Virus Hemagglutinin HA–2 N–Terminal Fusogenic Peptides Augment Gene Transfer by Transferrin–Polylysine–DNA Complexes: Toward a Synthetic Virus–Like Gene—Transfer Vehicle," *Proc. Natl. Acad. Sci.*, 89:7934–7938 (1992).

Wheatley et al., "pH–Dependent Pore Formation in Liposomes: An Approach to Triggered Release,"0 *Proc. Intern. Symp. Controlled Release of Bioactive Materials*, 21:600–601 (1994).

Winnik et al., "Pyrene–Labeled Amphiphilic Poly–(N–Isopropylacrylamides) Prepared by Using a Lipophilic Radical Initiator: Synthesis, Solution Properties in Water, and Interactions with Liposomes," *Can. J. Chem.*, 73:2030–2040 (1995).

Woodle et al., "Sterically Stabilized Liposomes," *Biochimica et Biophysica Acta*, 1113:171–199 (1992).

Wu et al., "Conjugation of Phosphatidylethanolamine to Poly(N–Isopropylacrylamide) for Potential Use in Liposomal Drug Delivery Systems," *Polymer*, 33:4659–4662 (1992).

* cited by examiner

PH-SENSITIVE, SERUM-STABLE LIPOSOMES

CROSS-REFERENCES TO RELATED APPLICATIONS

This case claims priority from U.S. Serial No. 60/073,471, filed Feb. 3, 1998, the contents of which are incorporated by reference.

STATEMENT AS TO RIGHTS TO INVENTIONS MADE UNDER FEDERALLY SPONSORED RESEARCH AND DEVELOPMENT

Not applicable.

FIELD OF THE INVENTION

This invention relates to the field of liposomes. In particular, this invention provides novel liposomes that are pH-sensitive, yet are also stable in serum. The invention further relates to methods of conferring pH sensitivity upon liposomes of varying compositions.

BACKGROUND OF THE INVENTION

A number of pharmaceutical agents and potential pharmaceutical agents suffer from poor aqueous solubility, high levels of antigenicity, toxicity, or rapid degradation in serum, which can hamper the development of suitable clinical formulations. One solution to these problems has been to encapsulate the pharmaceutical agent in a delivery vehicle that is soluble in aqueous solutions and that shields the agent from direct contact with tissues and blood. In particular, formulations based on liposome technology are of significant interest. Liposomes are vesicles comprised of concentrically ordered phopholipid bilayers which encapsulate an aqueous phase. They form spontaneously by hydrophobic interactions when phospholipids are exposed to aqueous solutions and can accommodate a variety of bioactive molecules.

Liposomes have proved a valuable tool as an in vivo delivery system for enhancing the efficacy of various pharmacologically active molecules (Ostro et al., *Liposomes-.from Biophysics to Therapeutics,* Dekker, New York, pp. 1–369 (1987)). Animal studies have shown that liposomes can decrease the toxicity of several antitumor and antifungal drugs, leading to clinical trials with promising results (Sculier et al., *Eur. Cancer Clin. Oncol.,* 24: 527–538; Gabizon, et al., *Eur. J. Cancer Clin. Oncol.,* 25: 1795–1803 (1989); Treat et al., *J. Nati. Cancer Inst.,* 82: 1706–1710 (1990); Lopez-Berestein et al., *J. Infect. Dis.,* 151: 704–710 (1985); Present et al., *Cancer,* 62: 905–911 (1988)). In addition, liposomes have been shown to be efficient carriers of antiparasitic drugs for treating intracellular infections of the reticuloendothelial system (RES), in activating macrophage cells to become tumoricidal, in models of metastasis, and in enhancing the immune response to encapsulated antigens, thus facilitating the formulation of artificial vaccines (*Liposomes in the Therapy of Infectious Diseases and Cancer,* Lopez-Berestein & Fidler, eds. Liss, New York (1989); Alving et al. *Immunol. Lett.,* 25: 275–280 (1990))

Numerous studies have reported on efforts to develop pH-sensitive liposomes as drug delivery systems (Collins, D. in: *Liposomes as Tools in Basic Research and Industry* (Philippot, J. R. and Schuber, F., Eds.) pp. 201–214, CRC Press, Boca Raton, Fla. (1995) (hereafter, "Collins 1995"); see also, Liu, D. et al., *Biochim. Biophys. Acta* 1022:348–354 (1990); Slepushkin, V. A. et al., *J. Biol. Chem.* 272:2382–2388 (1997)). Since liposomes are internalized by cells mainly via the endocytic pathway (Straubinger, R. M. et al., *Cell* 32:1069–1079 (1983)), whereby the liposomes are internalized and exposed to the lowered pH of an endosome, pH-sensitization of liposomes is an attractive strategy to facilitate the delivery of membrane impermeable drugs to the cytoplasm before lysosomal enzymatic degradation occurs. Unsaturated phosphatidylethanolamine ("PE") has been widely employed to confer intrinsic pH-sensitivity to liposomes.

At physiological pH in isotonic buffer, the equilibrium phase of unsaturated PE is the inverted hexagonal ($Hi_{II}$) phase (Cullis et al., *Biochim. Biophys. Acta* 559, 399–420 (1979); Tilcock, C. P. S et al., *Biochim. Biophys. Acta* 684,212–218 (1982); Allen et al., *Biochemistry* 29, 2976–2985 (1990)). Under these conditions, PE is protonated and unable to form bilayer ($L_a$) vesicles (Papahadjopoulos et al., *Biochim. Biophys. Acta* 135, 624–638 (1967)). The bilayer phase of unsaturated PE can, however, be stabilized by weakly acidic amphiphiles such as oleic acid (OA) (Straubinger et al., *FEBS Lett.* 179, 148–154 (1985)) or cholesterylhemisuccinate (CHEMS) (Ellens et al., *Biochemistry* 23, 1532–1538 (1984)), which confer a negative charge headgroup at pH 7.4. This charge provides electrostatic repulsion to block PE intermolecular interaction/interbilayer contact, thus preventing $H_{II}$ phase formation under physiological conditions. Protonation of the amphipile headgroup caused by a reduction of pH, neutralizes the negative charge and the vesicles become destabilized as the PE component reverts to the $H_{II}$ phase (Litzinger et al., *Biochim. Biophys. Acta* 11 13, 201–227 (1992). This is generally accompanied by the release of liposomal contents.

Although such liposomes have been shown to be efficient systems for cytoplasmic delivery in cultured cells (Collins 1995, supra), their moderate stability as well as their rapid clearance from the blood have hampered their in vivo use. Despite the fact that small unilamellar PE vesicles (SUV) have been found to be stable in plasma (Liu, et al., *Biochemistry* 28:7700–7707 (1989); Liu, et al., *Biochemistry* 29:3637–3643 (1990)), the extraction of the acidic amphipile by the plasmatic albumin results in the rapid loss of the pH-sensitivity. Leventis et al. (*Biochemistry* 26, 3267 (1987); 3276) and Collins et al. (*Biochim. Biophys. Acta* 1025, 234–242 (1990) (hereafter "Collins 1990")) demonstrated that the loss of the pH-sensitive moiety can be slowed down by using titratable double-chain amphiphiles such as 1,2-dipalmitoyl-sn-3-succinylglycerol (1,2-DPSG). It was found that although small dioleoylphosphatidylethanolamine (DOPE) liposomes containing 1,2-DPSG maintained their pH-sensitivity after incubation in plasma, there was a substantial shift of the destabilization pH from 5.3 to 4.2 (Collins 1990). Furthermore, after systemic administration, PE liposomes are rapidly cleared from the blood and accumulate in the lung, liver and spleen (Connor et al., *Biochim. Biophys. Acta* 884:474–481 (1986).

Colloidal stabilization of liposomes can be improved by inclusion of ganglioside ($GM_1$) or poly(ethylene glycol)-derivatized lipids (PEG-PE) (Papahadjopoulos, D. et al., in: *Liposomes as Tools in Basic Research and Industry* (Philippot, J. R. and Schuber, F., Eds.) pp. 177–188, CRC Press, Boca Raton, Fla. (1995)) (hereafter, "Papahadjopoulos, 1995"). These so-called "sterically stabilized liposomes" ("SSL,"or Stealth® liposomes) have shown long circulation half-lives, reduced uptake by the mononuclear phagocyte system and accumulation in tumors (Papahadjopoulos, 1995;

Woodle, M. C. et al., *Biochim. Biophys. Acata* 1113:171–199 (1992); Woodle, U.S. Pat. No. 5,356,633). Such coating of PE-based pH-sensitive liposomes increases their stability and circulation time in blood but simultaneously reduces their pH-sensitivity (Liu, D. et al., *Biochim. Biophys. Acta* 1022:348–354 (1990); Slepushkin, V. A. et al., *J. Biol. Chem.* 272:2382–2388 (1997)). To circumvent this drawback, the use of cleavable PEG-coating has recently been proposed (Kirpotin, D. et al., *FEBS Lett.* 388:115 . 118 (1997)).

Acid-triggered liposomes destabilization/fusion can be achieved extrinsically by using non-peptidic titratable synthetic polymers (Tirell, D.A. et al., *Ann. N. Y. Acad. Sci.* 446:237–248 (1985); Kono, K. et al., *Biochim. Biophys. Acta -b 1193:1–9* (1994)). The advantage of this approach is the potentiality to render different lipid-based formulations sensitive to pH, without the limitations associated with PE-based liposomes. Although fusogenic peptides can also trigger membrane disruption at acidic pH and have been successfully used to enhance the transfection efficiency of plasmid DNA (Wagner, E. et al., *Proc. Natl. Acad. Sci. USA* 89:7934–7938 (1992)), they display several disadvantages in the development of pH-sensitive liposomes including high cost of production, immunogenicity and non-trivial association to the liposome surface.

Several recent studies have shown that liposomes coated with copolymers of N-isopropylacrylamide (NIPA) bearing alkyl chains, acquire thermo-responsive properties (Wu, X.S. et al., *Polymer* 33:4659–4662 (1992) (hereafter "Wu, 1992"); Kono, K. et al., *J. Controlled Release* 30:69–75 (1994) (hereafter "Kono 1994"); Kim, J.C. et al., *J. Biochem.* 121:15–19 (1997) (hereafter "Kim 1997")). The alkyl substituent can interact strongly with the liposome membrane and serves as an anchor for the polymers onto the liposomes (Winnik, F. M. et al., *Can. J. Chem.* 73:2030–2040 (1995); Ringsdorf, H. et al., *Biochim. Biophys. Acta* 1153:335–344 (1993)). The homopolymer of NIPA is physically characterized by its lower critical solution temperature ("LCST"), which is around 32° C. in aqueous solutions (Heskins, M. et al., *J. Macromol. Sci. Chem.* 2:1441–1455 (1968); Feil, H. et al., *Macromolecules* 26:2496–2500 (1993)). The polymer is soluble below its LCST and separates from solution above it.

This temperature sensitivity was used to destabilize the lipid bilayer of liposomes and to induce the release of their contents in response to an increase in external temperature (Wu 1992; Kono 1994; Kim 1997). By randomly introducing a small amount of a pH-sensitive monomer in the structure of poly(NIPA), it is possible to increase its LCST above 37° C. and make the polymer pH-responsive (Taylor, L.D. et al. *D. J. Polym. Sci.* 13:2551–2570 (1975); Hirotsu, S. et al., *J. Chem. Phys.* 87:1392–1395 (1987); Chen, G. et al., *Nature* 373:49–52 (1995)). This property was, for instance, exploited in the preparation of pH-sensitive hydrogels containing cross-linked copolymers of NIPA for the controlled delivery of low molecular weight compounds (Dong, L. C. et al., *J. Controlled Release* 15:141–152 (1991)) and macromolecular drugs (Kim, Y. H. et al, *J. Controlled Release* 28:143–152 (1994); Brazel, C.S. et al,*J. Controlled Release* 29:57–64 (1996)). Hydrogels are, however, constituted of cross-linked polymers, and these finding therefore have no clear application to liposomes, which are formed instead by the hydrophobic interactions of lipid bilayers.

In another study, Wheatley, et al (*Proc. Intern. Symp. Control. Rel. Bioact. Mater.* 21:600–601 (1994)) changed the amount of poly(ethylacrylic acid) ("PEAA") in buffer containing liposome suspensions and reported that changing the amount of PEAA in the buffer caused corresponding changes in the percentage of leakage of liposomes in the suspension. This approach is not easily translated into in vivo use in a mammal since it would be difficult to maintain and control serum levels of PEAA adequate to act on liposomes (if, indeed, those levels were not themselves harmful to the mammal).

Thus, the art has not succeeded in solving the problem of how to create a pH sensitive liposome which can remain stable in the blood long enough to deliver its contents to target cells.

SUMMARY OF THE INVENTION

This invention relates to compositions of liposomes which as pH sensitive, yet serum stable. The invention further concerns the discovery of copolymers that can confer on liposomes, including sterically stabilized liposomes, the ability to release their contents upon a lowering of pH from normal physiological pH to a pH between about 3.5 and about 6.5.

The invention concerns pH sensitive, serum stable liposomes loaded with an agent and having a lipid bilayer, which comprise a thermally-sensitive polymer showing lower critical solution temperature behavior in an aqueous solution, said polymer bearing a hydrophobic substituent and a pH sensitive substituent, wherein said hydrophobic substituent is less than 10 kD and is selected from the group consisting of an alkyl compound and a hydrophobic polymer, which alkyl compound or hydrophobic polymer can insert into the lipid bilayer of the liposome, and further wherein the liposome, when in an aqueous solution, releases at least 20% of the agent upon a change in pH of the solution from pH 7.4 to pH 3.5.

The thermally-sensitive polymer can be NIPA, poly (N-substituted acrylamides, poly(N-acryloyl pyyrolidine), poly(N-acryloyl piperidine, a poly(acryl-L-amino acid amide), a poly(vinyl alcohol) derivative, poly(ethyl oxazoline), hydroxypropyl acrylate, hydroxypropyl cellulose, hydroxyethyl cellulose, polyvinyl acetate phthalate, hydroxypropyl methylcellulose acetate succinate, methylcellulose, hydroxymethyl cellulose, and cellulose.

The alkyl compound can be ODA, a double alkyl chain lipid, or phosphatidylethanolamine. The pH sensitive moiety can be a titratable acidic polymer. In particular, it can be an alkylacrylic acid. Preferred alkylacrylic acids are methylacrylic acid, ethylacrylic acid, propylacrylic acid, and butylacylic acid. The alkylacrylic acid can be present at a mol % of between about 0.5% and about 10%. The liposome can contain PEG. In a preferred embodiment, the thermally-sensitive polymer is NIPA, the alkyl compound is ODA, and the pH sensitive moiety is MAA. Preferred molar ratios of these three molecules are about 94:5:1, about 93:5:2, or about 91:5:4.

The liposome can comprise molecules selected from the group consisting of DSPC, POPC, HSPC, EPC, and EPC/ Chol/PEG-PE. In a preferred embodiment, the EPC/Chol/ PEG-PE molecules are present in a molar ratio of about 3:2:0.3. The liposomes can be stabilized with PEG, or with ganglioside-derivatized lipids, or with another hydrophilic polymer that stabilizes the liposome and which increases the half life of the liposome in the bloodstream.

The liposome can be loaded with an agent selected from the group consisting of a drug, a radioisotope, a detectable label, a nucleic acid, a vector, and a ribozyme.

The invention further includes methods of delivering an agent to a cell comprising contacting a cell with a liposome of those described above, wherein the liposome is loaded with the agent. The contacting can be caused by systemic administration of the drug. Preferred forms of systemic administration are by injection and by intravenous administration.

The invention further relates to a method of conferring pH sensitivity on, or increasing the pH sensitivity of, a liposome having a lipid bilayer. The method includes the step of complexing the liposome with a thermally-sensitive polymer showing lower critical solution temperature behavior in aqueous solutions, said thermally-sensitive polymer bearing a hydrophobic substituent and a pH sensitive substituent, wherein said hydrophobic substituent is less than 10 kD and is selected from the group consisting of an alkyl compound and a hydrophobic polymer, which alkyl compound or hydrophobic polymer can insert into the lipid bilayer of the liposome, and further wherein the liposome, when in an aqueous solution, releases at least 20% of the agent upon a change in pH of the solution from pH 7.4 to pH 3.5.

The thermally-sensitive polymer can be selected from the group consisting of can be NIPA, poly (N-substituted acrylamides, poly(N-acryloyl pyyrolidine), poly(N-acryloyl piperidine, a poly(acryl-L-amino acid amide), a poly(vinyl alcohol) derivative, poly(ethyl oxazoline), hydroxypropyl acrylate, hydroxypropyl cellulose, hydroxyethyl cellulose, polyvinyl acetate phthalate, hydroxypropyl methylcellulose acetate succinate, methylcellulose, hydroxymethyl cellulose, and cellulose.

The alkyl compound can be ODA, a double alkyl chain lipid, or phosphatidylethanolamine. The pH sensitive moiety can be a titratable acidic polymer. In particular, it can be an alkylacrylic acid. Preferred alkylacrylic acids are methylacrylic acid, ethylacrylic acid, propylacrylic acid, and butylacrylic acid. The alkylacrylic acid can be present at a mol % of between about 0.5% and about 10%. The liposome can contain PEG. In a preferred embodiment, the thermally-sensitive polymer is NIPA, the alkyl compound is ODA, and the pH sensitive moiety is MAA. Preferred molar ratios of these three molecules are about 94:5:1, about 93:5:2, or about 91:5:4.

The liposome can contain an agent selected from the group consisting of a drug, a radioisotope, a detectable label, a nucleic acid, a vector, and a ribozyme.

The liposome can comprise molecules selected from the group consisting of DSPC, POPC, HSPC, EPC, and EPC/Chol/PEG-PE. In a preferred embodiment, the EPC/Chol/PEG-PE molecules are present in a molar ratio of about 3:2:0.3.

DETAILED DESCRIPTION

A. Definitions

Figure 1:
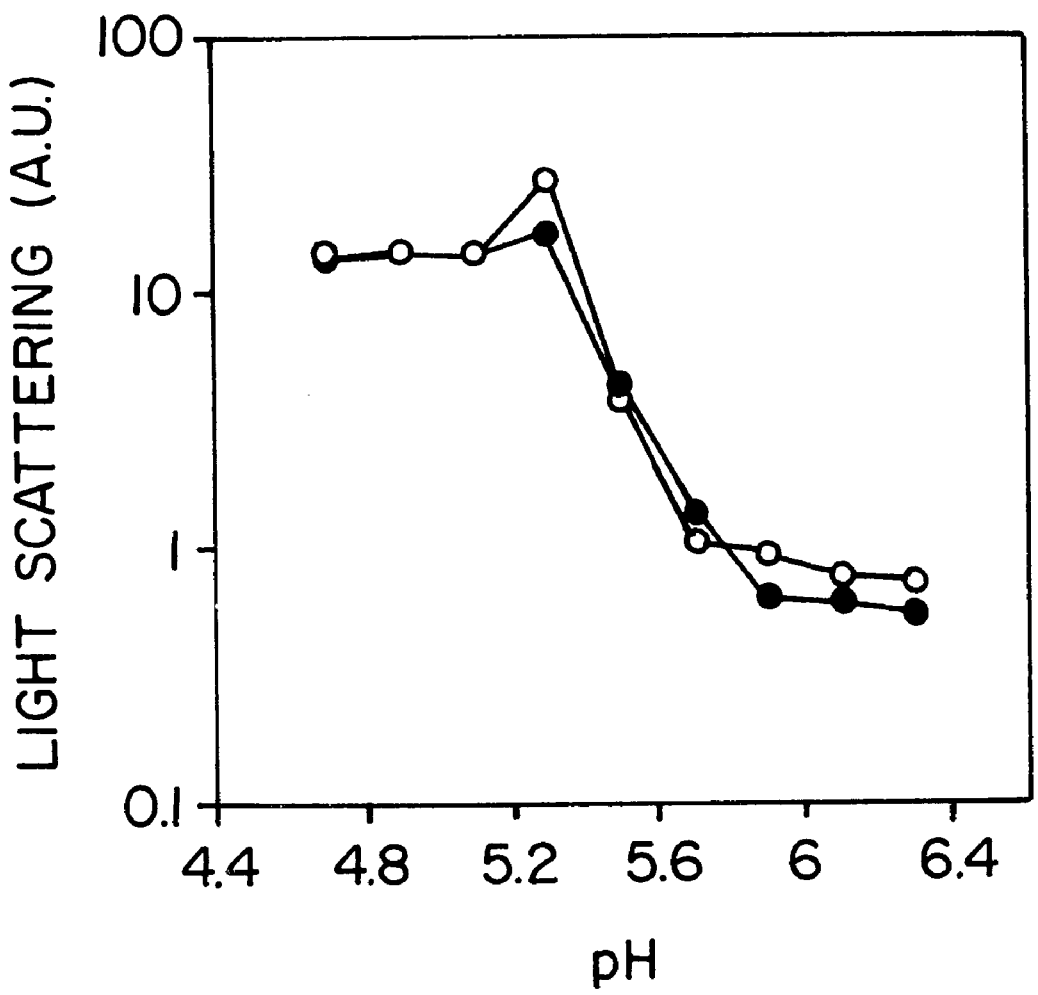
FIG. 1. Solubility of poly(NIPA-co-MAA) (closed circles) and poly(NIPA-co-MAA-co-ODA) (open circles) at 37° C. in MES buffer, as a function of pH. Polymer concentration was 45 µg/mL.

The following abbreviations are used herein: AIBN, 2,2'-azobisisobutyronitrile; $C_{12}E_8$, octaethyleneglycol dodecyl ether; Chol, cholesterol; DPX, p-xylene-bis-pyrimidium bromide; DSPE, 1,2-distearoyl-sn-glycero-3-phosphatidylethanolamine; EPC, egg phosphatidylcholine; HBS, HEPES-buffered saline (20 mM HEPES-Na, 144 mM NaCl, pH 7.2); HEPES, N-(2-hydroxyethyl)-piperazine-N'-(2-ethane sulfonic acid); HPTS, trisodium 8-hydroxypyrene trisulfonate; LCST, lower critical solution temperature; MAA, methacrylic acid; MES, 2-N-(morpholino)ethane-sulfonic acid; NIPA, N-isopropylacrylamide; ODA octadecyl acrylate; PEG-PE, N-(ω-methoxypoly(oxyethylene)-α-oxycarbonyl)-DSPE (note: PEG-PE directly refers only to poly(ethylene glycol) (the "PEG" moiety)-phosphatidylethanolamine (the "PE" moiety). The molecule is, however, the head group of a phospholipid which also includes two acyl chains. By convention, these are not usually referred to or specified, but are understood by those of skill in the art to be included); SSL, sterically stabilized liposomes; GMI, ganglioside; POPC, 1-palmitoyl-2-oleoyl-sn-glycero-3-phosphatidylcholine; DSPC, 1,2-distearoyl-sn-glycero-phosphatidylcholine-1,1,2,2-d4; HSPC, hydrogenated soy phosphatidylcholine; NBD-PE, N-(7-nitro-2,1,3,-benzoxadiazol-4-ly)phosphatidylethanolamine; Rh-PE, N-(lissamine rhodamine B sulfonyl) phosphatidylethanolamine; RES, reticuloendothelial system (also known as the "mononuclear phagocytic system").

The terms "ligand" or "targeting moiety," as used herein, refer generally to all molecules capable of specifically binding to a particular target molecule and forming a bound complex. Thus, the ligand and its corresponding target molecule form a specific binding pair. Examples include, but are not limited to, antibodies, lymphokines, cytokines, receptor proteins such as CD4 and CD8, solubilized receptor proteins such as soluble CD4, hormones, growth factors, and the like, which specifically bind desired target cells, and nucleic acids, which bind corresponding nucleic acids through base pair complementarity. Particularly preferred targeting moieties include antibodies and antibody fragments (e.g., the Fab' domain).

A "pharmaceutically acceptable carrier" is a material that is not biologically or otherwise undesirable, i.e., the material can be administered to an individual along with the liposome without causing any undesirable biological effects or interacting in a deleterious manner with any of the other components of the pharmaceutical composition in which it is contained.

The terms "mole percent" (also written "mol %"), and "molar ratio," refer to the percent of a component on a molar scale. When they refer to components of a liposome, they are is expressed relative to the total lipid in the liposome unless otherwise stated. Thus, for example, in a liposome comprising a ratio of phosphatidylcholine (PC) to Chol of 150:100, 4 mole percent of hydrophilic polymer (i.e., PEG) would represent a ratio of PC:Chol:PEG of about 150:100:10. When they refer to the components of a polymer, they refer to the molar ratio of the respective components. Ratios of polymers used in herein refer to molar ratios. For example, a polymer of NIPA, MAA, and ODA of 93:5:2 refers to a polymer in which 93 moles of NIPA are present for each 5 moles of MAA and each 2 moles of ODA.

The term "serum-stable" as used herein refers to a liposome which is more stable in mammalian blood serum or plasma (such as fetal calf serum, bovine serum, horse serum, or human blood serum or plasma) than are liposomes consisting of egg phosphatidylcholine. Preferably, a "serum-stable" liposome is at least twice as stable as a liposome of egg phosphatidylcholine in human blood serum or plasma at physiological pH (generally considered to be a pH of 7.4) and 37° C., as measured by the time required for the liposome to leak (or release) a given percentage of its contents. Exemplar methods for measuring loss of liposome contents are given in the Examples, infra.

The term "pH sensitive" as used herein refers to a molecule which changes in conformation or other properties in response to changes in pH of the surrounding environment. As used herein, the term further refers to a molecule whose conformation or properties changes as pH decreases from 7.4 to 3.5–6.5.

The term "thermally-sensitive" as used herein refers to a molecule which changes in conformation or properties in response to changes in environmental temperature. As used herein, the term refers to molecules which exhibit such changes with the range of 30° to 50° C.

The term "lower critical solution temperature" generally refers to the basic thermodynamics of mixtures of polymers, and represents the lower point at which two polymers separate into two phases. See generally, Kroschwitz, ed, *Kirk-Othmer Encyclopedia of Chemical Technology* John Wiley & Sons New York 19:837–904 ($4^{th}$ ed., 1996); Hoffman, A. "Intelligent Polymers" in Park, K, ed., *Controlled Drug Delivery: Challenges and Strategies,* American Chemical Soc., Washington, D.C. (1997). As used herein, it means the temperature at which a polymer (whether a homopolymer or a heteropolymer) undergoes phase transition from soluble to insoluble. Specifically, below the LCST, the polymer is soluble in water and, above it, the polymer precipitates from the solution.

The term "polymer," as used herein, can mean a homopolymer or a heteropolymer. Thus, it can, as appropriate, encompass copolymers (wherein two polymers are mixed) and terpolymers (polymers of three constituents). The invention relates to rendering liposomes pH sensitive using polymers containing three constituents: a thermally-sensitive polymer (which is present in the largest molar ratio of the three), an alkyl compound or hydrophobic polymer which serves to anchor the thermally-sensitive polymer to the liposome, and a pH sensitive moiety. Most commonly, the term polymer is used herein to refer to the thermally-sensitive polymer. It is, however, sometimes used to refer to a combination of the thermally-sensitive polymer with one or both of the other components, particularly when emphasizing the combination of the components. The particular meaning will be clear in context.

The term "clearance half life" refers to uptake by the reticuloendothelial system (RES) of liposomes circulating in the bloodstream. Specifically, the term refers to the time it takes the RES to remove (or clear) one half of a group of liposomes from the circulation. Assays for determining the half life of liposomes in the circulation are taught in Section J, below.

The term "load," used in relation to a liposome, refers to encapsulating an agent, such as a drug, label, or radioisotope, within a liposome.

B. Description of the Invention
1. The Invention

The present invention provides pH sensitive liposomes which are stable in the serum. Surprisingly, it further provides a means of conferring pH sensitivity to any liposome, whether previously thought to be stable or unstable in blood serum. It thus provides a substantial advance in the art of liposome formulation, and sharply increases the ability of liposomes to deliver agents to cells in in vitro and in vivo applications.

The pH sensitive liposomes of the invention release a larger proportion of their contents than do non-pH sensitive liposomes when the pH of the surrounding environment decreases from physiological pH (pH 7.4) to a pH between about 3.5 and 6.5. This characteristic can be exploited to advantage for in vitro and in vivo uses. As noted in the Background section, liposomes are internalized by cells via the endocytic pathway, and are exposed in the endosome to a decreasing pH. Since liposomes can be targeted to cells using appropriate ligands such as antibodies directed to epitopes on cells of interest, a liposome stable at pH 7.4 but unstable at a pH encountered in the endosome can be used to deliver its contents preferentially to the targeted cell population. Further, since many tumors tend to have a pH of between 5.8 to 6.5, liposomes stable at pH 7.4, but destabilized at a pH of 5.8–6.5, can be used to deliver cytotoxic agents, imaging agents, or other desired agents preferentially to tumor cells. The liposomes of the invention are preferred for targeting agents to tumors which are more acidic than surrounding normal tissue, such as tumors with a pH of about 6.5 or less, and even more preferably those with a pH of about 6 or less.

Sensitivity to pH can be conferred upon liposomes by use of a copolymer of: a thermally-sensitive polymer with a lower critical solution temperature in aqueous solution, an alkyl compound or hydrophobic polymer with a molecular weight below about 10 kD to anchor the thermally-sensitive polymer to the liposome, and small amounts (10% or less) of a pH sensitive (ionizable) moiety, such as an alkylacrylic acid, or a polymer to respond to changes in the pH of the environment and to impart those changes to the thermally-sensitive polymer. Each of these components of the copolymer will be discussed in some detail in later sections.

The invention has significant advantages over previous approaches to creating pH sensitive liposomes. First, simply using high amounts of pH sensitive polymers, which might seem to be the most straightforward approach, is undesirable since such polymers are charged, and confer a proportionally large charge upon the liposome. Charged molecules are typically more quickly removed from the systemic circulation by the RES. Thus, it is desirable to confer pH sensitivity upon liposomes in a manner which does not result in the liposome carrying a high density of charge.

In the compositions of the invention, the pH sensitive moiety is present in small quantities compared to the other components of the copolymer and the thermally-sensitive polymer is hydrophilic. These compositions have increased circulation times (longer half lives) in the bloodstream than do comparable liposomes without the copolymers. In particularly preferred embodiments, the liposomes of the invention have half lives in the circulation of one hour or more (assays for determining the time required for clearance of liposomes from the circulation are discussed in Section J, below).

Preferably, the amount of pH sensitive moiety is less than 20 mol % of the composition, and more preferably is about 15 mol % or less. Even more preferably, it is about 10 mol % or less, and most preferably is about 5 mol % or less. It is part of the present invention that these relatively modest amounts of pH sensitive molecules can confer pH sensitivity to the liposome when used in conjunction with the other components of the copolymer.

Second, previous studies have shown some release of liposome contents with various formulations of polymers. The present invention improves the release of liposome contents, and permits modulation of liposome release over a wide range of liposome formulations. Preferably, the release of liposome contents exceeds about 20% with liposome compositions which are considered stable in the serum. More preferably, about 25% or more of the contents are released, and even more preferably, about 30% or more of the contents are released.

Third, the polymer coatings disclosed herein can be adapted for any liposome, including fluid, rigid (sometimes called "solid"), or SSL liposomes. The release of contents of these liposomes can be altered by use of appropriate polymer coatings. For example, we have demonstrated the ability of polymers of the invention to induce release of the contents of liposomes which had a high phase transition. These rigid liposomes, which are stable and normally do not leak their contents under the conditions under which they were tested, nonetheless were shown to release substantial portions of their contents upon a decrease in the environmental pH. Further, intrinsically pH sensitive liposomes can have their pH sensitivity increased, while increasing their stability in serum or plasma. Accordingly, the invention provides a means for modulating liposome response to pH within physiologically relevant ranges (i.e., as pH decreases from pH 7.4 to a range of about 3.5 to about 6.5, more preferably to a range of about 3.5 to about 6.0, and, even more preferably, as it decreases from 7.4 to a range from about 3.5 to about 5.5).

Fourth, for both in vitro and in vivo uses, it is desirable that the polymer coatings used to confer pH sensitivity are not themselves acutely toxic. Exemplar polymers have been tested in in vitro cellular tests and in in vivo studies in mice. To date, no acute toxicity has been noted.

Fifth, and finally, the presence of the polymer coating should not adversely affect the ability of the liposomes to reach the organs or tissues to be targeted to an extent that the liposomes are no longer capable of delivering significant amounts of desired agents to the target organs or tissues. In in vivo biodistribution studies with exemplar polymers in nude murine bearing human breast tumor, the distribution of SSL liposomes bearing pH-sensitive polymer reaching the various organs sampled showed some variation from the distribution of SSL not bearing such a polymer. Despite this variation, however, the liposomes still showed a significant accumulation in the tumor cells. Further, in in vitro studies reported in Example 3, cancer cells overexpressing a receptor for folate took up folate-targeted liposomes bearing an exemplar polymer coating. Accordingly, both in vivo and in vitro results have demonstrated that polymer coats can confer pH sensitivity to liposomes without eliminating the ability of the liposomes to deliver significant amounts of agents to target cells.

2. In vitro and ex vivo Uses of the Invention

Most animal cells, including human cells, are cultured in media containing serum. Common sera used in cell and tissue culture include calf, fetal bovine, horse, and human. See e.g., Freshney, R. I., *Culture of Animal Cells,* Wiley-Liss, Inc. New York (3$^{rd}$ Ed., 1994). Thus, it is desirable that liposomes used to deliver agents to cells in cell or tissue culture are stable in serum even though they are not being used within a body.

Liposomes of the invention can be used in vitro for a variety of purposes. For examples, liposomes can be used to carry into cultured cells drugs or other agents which are otherwise difficult to get through biological membranes. Such agents can include large molecular weight compounds, compounds which would be affected by plasma proteases, nucleases, or other enzymes, and compounds which would otherwise not be readily transported across the cell membrane. In one preferred embodiment, the liposomes bear ligands overexpressed by cancer cells and contain a cytotoxic agent. In this embodiment, the liposomes preferentially bind to any cancer cells in the cultured population, are internalized, and kill the cancer cells. Thus, the liposomes of the invention can be used to purge a cultured cell population of any cancer cells bearing a marker which distinguishes those cells from the general cell population. If desired, the cells remaining after the cancer cells have been eliminated or reduced in number can be infused into a patient in need thereof. For example, bone marrow cells taken from a patient can be purged of cancer cells ex vivo and the remaining cells can be reinfused into the patient. The Examples demonstrate the delivery of a widely-used anti-cancer agent, doxirubicin, to human cancer cells.

The liposomes can be used to transfect targeted cells with nucleic acids. The nucleic acids can encode useful proteins, and the resulting cells can be cultured to produce the proteins in quantity. Alternatively, the nucleic acids can encode a protein missing from the cells to add a new functionality or to correct the absence of a missing functionality. Cells so transfected can be reintroduced into the organism from which they were extracted, or further maintained in culture. Similarly, the nucleic acids can be, or can encode, ribozymes to cleave any target sequences which might be present in the transfected cells. In one embodiment, the nucleic acids can encode ribozymes directed against a virus such as HIV. The ribozymes can eliminate or reduce any virus present in the transfected cells. In preferred embodiments, the ribozyme is co-transfected with a detectable marker or a nucleic acid encoding a detectable marker, to ease detection of and selection for the transfected cells. The liposome can further carry nucleic acids which are antisense oligonucleotides, designed to bind to and thereby inactivate undersirable nucleic acid sequences in the target cells.

3. In vivo Uses

The liposomes of the invention also have a number of in vivo uses. The liposomes can be used to deliver therapeutic and other agents to particular cell populations targeted by appropriate ligands. In particular, liposomes can be used to protect agents which would be destroyed or inactivated if introduced free in the circulation (such as proteins or nucleic acids which would be affected by endogenous proteases or nucleases, respectively), or to carry into cells agents which have properties, such as ionic charge, which would result in their rapid clearance from the systemic circulation or prevent their passage through cell membranes.

The liposomes can also be used to deliver high local concentrations of agents to tumors extracelluarly. Tumors often are characterized by existing in an environment of lower than normal pH, wherein the pH ranges from 7 to 5.8. Liposomes of the invention may be used to deliver agents to tumors existing at pHs of 6.5 or below. The lower pH level of the area around the tumor serves to trigger extracellular release of a substantial portion of the contents of the liposome, resulting in a high localized concentration of the agent. This more localized delivery of, for example, cytotoxic agents, permits delivery of agents to the tumor sites with lessened systemic effects of the agent on the patient.

In preferred embodiments, the liposomes carry ligands or antibodies appropriate for targeting the liposome to cancer cells, and are used to deliver cytotoxic agents to those cells, which then internalize the liposomes. The Examples demonstrate the delivery of the contents of liposomes of the invention to human cancer cells to which they were targeted by means of a ligand to a receptor overexpressed on many cancer cells.

C. Liposome Composition

1. Liposomes

Liposomes are lipid vesicles. In general, the liposomes of the invention comprise one or more vesicle-forming lipids which form a lipid bilayer. The liposomes further comprise a thermally-sensitive polymer having a LCST in aqueous solution, bearing an alkyl compound or hydrophobic polymer to anchor the thermally-sensitive polymer to the liposome, and a pH sensitive moiety to confer pH sensitivity to the overall polymer, and thus to the liposome. Optionally, the liposome further bears additional polymers to modulate the pH or thermal sensitivity of the liposome, or an antibody, ligand, or other targeting moiety to direct the liposome to target cells, or both. The liposome will usually be "loaded" with an agent intended to reach the interior of target cells.

2. Vesicle-forming Lipids

The vesicle-forming lipid is preferably one having two hydrocarbon chains, typically acyl chains and a polar head group. Included in this class are the phospholipids, such as phosphotidylcholine (PC), phophotidylethanolamine (PE), phosphatidic acid (PA), phophotidylinositol (PI), and sphingomyelin (SM), where the two hydrocarbon chains are typically about 14–22 carbons in length and have varying degrees of unsaturation or 14–18 carbon chain saturated phospholipids. Also included in this class are the glycolipids, such as cerebrosides and gangliosides.

In a preferred embodiment, the liposomes are SSL. For example, the liposomes can be derivatized with GM, or PEG-PE. In a particularly preferred embodiment, the liposomes are composed of EPC/Chol/PEG-PE (particularly in a 3:2:0.3 molar ratio). Methods of derivatizing liposomes with GMI or PEG-PE are discussed in Section G, below.

Liposomes useful in the invention may also be composed of sphingomyelin or phospholipids with head groups such as ethanolamine, serine, glycerol, and inositol. In particular, phospholipids suitable for formation of liposomes useful in the methods and compositions of the invention include, e.g., PC, PE, PI, PA, lecithin, cephalin, cardiolipin, cerebrosides, dicetylphosphate, dioleo-PC, dipalmitoyl-PC, dipalmitoyl-PE, and the like. Additional lipids suitable for use in the liposomes of the invention are well known to persons of skill in the art and are cited in a variety of sources, such as 1998 *McCutcheon's Detergents and Emulsifiers* and 1998 *McCutcheon's Functional Materials,* both published by McCutcheon Publishing Co., New Jersey.

According to one feature of the invention, the vesicle-forming lipid preferably is a relatively fluid lipid, meaning that the lipid has a relatively low liquid to liquid-crystalline melting temperature, e.g., at or below body temperature. The vesicle-forming lipid can also be a relatively rigid lipid, meaning that the lipid has a relatively high melting temperature, e.g., up to about 60° C. As a rule, the more rigid (i.e., saturated) lipids contribute to membrane rigidity in a lipid bilayer structure and also contribute to greater bilayer stability in blood. Other membrane components, such as cholesterol, are also known to contribute to membrane rigidity and stability in lipid bilayer structures. Long chain (e.g., $C_{14}$–$C_{22}$) saturated lipids plus cholesterol and SSL are preferred compositions for delivering agents to cells of interest since these liposomes do not tend to release their contents into the plasma as they circulate through the blood stream. Phospholipids whose acyl chains have a variety of degrees of saturation can be obtained commercially or prepared according to standard methods. See, e.g., Small. D. *The Physical Chemistry of Lipids,* Plenum Press, NY (1986).

In a preferred embodiment, PEG-PE is used to increase the stability of liposomes in serum or plasma. To provide adequate stability, it is desirable that the liposome contain about 4 mol % or more of PEG-PE. More preferably, the liposome should contain about 5 mol % or more of PEG-PE, and most preferably, it should contain about 6 mol %.

D. Thermally-Sensitive Polymers

Thermally-sensitive polymers having an LCST in aqueous solution are well known in the art. See, e.g., Hoffman, A. "Intelligent Polymers" in Park, K, ed., *Controlled Drug Delivery: Challenges and Strategies,* American Chemical Soc., Washington, D.C. (1997). These polymers show fairly large physical changes (or transitions) in response to temperature, and have as a common property a balance of hydrophilic and hydrophobic groups. A thermally induced phase separation causes the release of hydrophobically bound water, and a resulting change in the conformation and properties of the polymer. The combination of a thermally sensitive polymer with a pH sensitive component can make the thermally-sensitive polymer sensitive to pH changes because the ionization, and thus hydrophilicity, of the pH-sensitive component can be changed by changing the pH. In the uses contemplated for the invention, the physical changes in the conformation of the thermally-sensitive polymer, when coupled to a pH sensitive moiety, will be due to pH changes in the environment of the liposome.

In preferred embodiments, the thermally-sensitive polymers having an LCST in aqueous solutions have a small charge and a sharp phase transition, on the order of about 2–7° F., and more preferably about 2–4° F. A sharp phase transition helps assure that the contents of a liposome coated with the copolymers are not released before the pH reaches its intended level (that is, that the contents are not released, prematurely, into the serum or plasma). Further, it is preferable if the thermally-sensitive polymer has a phase transition of between about 30° C. and 50° C., and more preferably between about 30° C. and about 40° C. Preferably, the polymer is hydrophilic.

Preferred polymers are poly (N-substituted acrylamides, poly(N-acryloyl pyyrolidine), poly(N-acryloyl piperidine, poly(acryl-L-amino acid amides), poly(ethyl oxazoline), poly(vinyl alcohol) derivatives, hydroxypropyl acrylate, hydroxypropyl cellulose, hydroxyethyl cellulose, polyvinyl acetate phthalate, hydroxypropyl methylcellulose acetate succinate, methylcellulose, hydroxymethyl cellulose, or cellulose. Of these compounds, compounds with sharper phase transitions are preferred. In a particularly preferred embodiment, the polymer is NIPA.

E. Alkyl Compounds and Hydrophobic Polymer Anchors

When used in the compositions and methods of the invention, the thermally-sensitive polymers discussed above bear an alkyl compound or hydrophobic polymer. These moieties interact with the lipid bilayer of the liposome and serve to "anchor" the thermally-sensitive polymer to that bilayer (for convenience of reference, these moieties are sometimes referred to herein as the "anchor moiety"). Without being bound by any particular theory, the anchor appears to play a role in the ability of the thermally-sensitive polymer to destabilize the lipid bilayer and it is the change in the conformation of the thermally-sensitive polymer which destabilizes the liposome These changes create "point defects," or spaces in the bilayer that can disrupt the integrity of the bilayer around the anchor moiety. If the liposome has been previously loaded with an agent small enough to pass through any gaps in the bilayer due to this disruption, the agent will be able to leak into the environment surrounding the liposome.

The anchor moiety can be an alkyl compound or a hydrophobic polymer. The alkyl compound can be a single or double chain alkyl compound. In a preferred embodiment, the alkyl compound is phosphatidylethanolamine. In preferred embodiments the alkyl group is of $C_{14}$ to $C_{22}$. In the most preferred embodiment, the alkyl compound is ODA. The anchor moiety can also be a hydrophobic polymer. The hydrophobic polymer should be capable of inserting into the lipid bilayer and of attachment (i. e, covalent binding) to the thermally-sensitive polymer.

The anchor moiety should not be larger than about 10 kD, preferably is about 5 kD or less, and more preferably is smaller than about 1 kD. The anchor by itself should not destabilize the liposome the liposome at physiological pH (7.4), as measured by the leakage assays taught in the Examples. Further, the anchor should not be toxic by itself or in conjunction with the thermally-sensitive polymer. The anchor moiety need generally be present only in small quantities. Examples 1 and 2 demonstrate effective anchoring of the polymer to liposomes using ODA at 1 and at 2 mol %, respectively. Above 4 mol % of ODA, the composition gets harder to handle. Accordingly, in preferred embodiments, the anchor moiety is generally present at about 5 mol % or less. The amount of ODA will be varied, however, depending on the thermally-sensitive polymer with which it is to be employed. A more hydrophilic thermally-sensitive polymer will need less of the alkyl compound or hydrophobic polymer to anchor it to the liposome than will a hydrophobic thermally-sensitive polymer.

The mol % of alkyl compound or hydrophobic polymer to use with any particular thermally-sensitive polymer can conveniently be determined by incubating copolymers of thermally-sensitive polymer, a pH sensitive moiety, and differing mol %s of the alkyl compound or hydrophobic polymer with liposomes and performing liposome content release assays (described in the Examples and elsewhere herein) and ascertaining the copolymer which results in the release of the highest percentage of the contents of the liposome. The mol % of the alkyl compound or hydrophobic polymer resulting in the highest percentage of release is the best mol % to use with that particular thermally-sensitive polymer.

F. ph Sensitive Moieties

Finally, the polymer coating the liposomes should contain small quantities of a pH sensitive moiety to confer pH sensitivity to the overall polymer. Such moieties are ionizable, and therefore carry a charge. Preferred pH sensitive moieties are titratable acidic polymers. In preferred embodiments, the pH sensitive moiety is an alklyacrylic acid, such as ethylacrylic acid, propylacrylic acid, butylacrylic acid, and the like. The most preferred is methylacrylic acid.

Relatively small amounts of the pH sensitive moiety are needed to confer pH sensitivity upon the overall polymer. The Examples demonstrate the use of 5 mol % of MAA to confer pH sensitivity. The pH at which the polymer will cause the liposome to leak some of its contents can be modulated by changing the proportion of the pH sensitive moiety. To decrease the pH of release, the proportion of the pH sensitive moiety should be increased. Because of the charge on the pH sensitive moiety, however, the amount of pH sensitive moiety which should be used should not exceed 10 mol %. It should be noted that the pH of the endosome is about 4.5 to 5.5, and that of the later lysosome is about 3.5 to 4.5. Thus, the lowest pH as to which release of liposomal contents is contemplated is 3.5

When using MAA, satisfactory results can be obtained using between about 2 and about 5 mol %. When using pH sensitive monomers or moieties more hydrophobic than MAA, the proportion of the monomer or moiety may should be increased by one or more mol % to achieve an equivalent phase transition release. Additionally, the phase transition release can be modulated by adding additional hydrophobic or hydrophilic monomers to the polymer. The phase transition release (pH sensitivity) of the resulting polymers can be easily tested by coating liposomes with the polymers (as taught in the exemplar procedures set forth in the Examples), placing the liposomes in an aqueous solution, decreasing the pH of the solution to a pH of interest, and determining the percentage of contents of the liposomes released at that pH.

G. Preparation and Derivatiztion of Liposomes

A variety of methods are available for preparing liposomes as described in, e.g., Szoka et al., *Ann. Rev. Biophys. Bioeng.* 9:467 (1980); U.S. Pat. Nos. 4,186,183, 4,217,344, 4,235,871, 4,261,975, 4,485,054, 4,501,728, 4,774,085, 4,837,028, 4,946,787; PCT Publication No. WO 91/17424; Szoka & Papahadjopoulos, *Proc. Natl. Acad. Sci. (USA),* 75: 4194–4198 (1978), Deamer and Bangham, *Biochim. Biophys. Acta,* 443: 629–634 (1976); Fraley, et al., *Proc. Natl. Acad. Sci. USA,* 76: 3348–3352 (1979); Hope, et al., *Biochim. Bioshys. Acta,* 812: 55–65 (1985); Mayer, et al., *Biochim. Bioshys. Acta,* 858: 161–168 (1986); Williams, et al., *Proc. Natl. Acad. Sci. (USA),* 85: 242–246 (1988), the text *Liposomes,* Marc J.Ostro, ed., (Marcel Dekker, Inc., New York, 1983, Chapter 1), and Hope, et al., *Chem. Phys. Lip.* 40: 89 (1986), all of which are incorporated herein by reference.

Suitable methods include, e.g., sonication, extrusion, high pressure/homogenization, microfluidization, detergent dialysis, calcium-induced fusion of small liposome vesicles, and ether-infusion methods, all well known in the art. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents such as deoxycholate. In a preferred embodiment, multilamellar liposomes are produced by the reverse phase evaporation method of Szoka & Papahadjopoulos, *Proc. Natl. Acad. Sci. USA,* 75: 4194–4198 (1978).

Unilamellar vesicles are generally prepared by sonication or extrusion. Sonication is generally performed with a tip sonifier, such as a Branson tip sonifier, in an ice bath. Typically, the suspension is subjected to several sonication cycles. Extrusion may be carried out by biomembrane extruders, such as the Lipex Biomembrane Extruder. Defined pore size in the extrusion filters may generate unilamellar liposomal vesicles of specific sizes. The liposomes may also be formed by extrusion through an asymmetric ceramic filter, such as a Ceraflow Microfilter (Norton Co., Worcester Mass.).

Following liposome preparation, the liposomes which have not been sized during formation may be sized to achieve a desired size range and relatively narrow distribution of liposome sizes. A size range of about 0.2–0.4 microns allows the liposome suspension to be sterilized by filtration through a conventional filter, typically a 0.22 micron filter. The filter sterilization method can be carried out on a high through-put basis if the liposomes have been sized down to about 0.2–0.4 microns.

Several techniques are available for sizing liposomes to a desired size. Exemplar sizing methods are described in U.S. Pat. Nos. 4,529,561 and 4,737,323. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, Ann. Rev. Biophys. Bioeng., 10:421–450 (1981), incorporated herein by reference. Average liposome diameter may be reduced by sonication of formed liposomes. Intermittent sonication cycles may be alternated with QELS assessment to guide efficient liposome synthesis.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size. For use in the present invention, liposomes having a size of about 0.05 microns to about 1.5 microns are preferred. More preferred are liposomes having a size of about 0.05 microns to about 1.0 micron. Most preferred are liposomes have a size of about 0.05 to about 0.5 microns.

Liposomes may be derivatized with PEG, as taught in Woodle, U.S. Pat. No. 5,013,556 and Fisher, European Patent Specification Publication No. 0 445 131 B1, or with gangliosides, to increase their half life in the circulation. (See also, Papahadjopoulos, 1995; Woodle, M. C. et al., Biochim. Biophys. Acata 1113:171–199 (1992); Woodle, U.S. Pat. No. 5,356,633). When using the copolymers of the invention (thermally-sensitive polymer, alkyl compound or hydrophobic polymer, and pH sensitive moiety) of a high molecular weight in connection with these derivatized lipids, it is preferable to include the copolymers during the preparation of the liposomes than to incubate the derivatized liposomes with the copolymer later.

Alternatively, if a high molecular weight copolymer is to be incubated with the liposomes after they have been prepared, the mol % of the alkyl compound or hydrophobic polymer should be increased to assist in the binding of the copolymer to the liposome. A copolymer containing 2 mol % of ODA added during preparation of the liposome, for example, resulted in about as high a percentage of release of contents from those liposomes as seen using liposomes incubated after their preparation with a like copolymer containing 4 mol % of ODA. Unlike some previous studies, we have confirmed by labeling studies that the copolymers of the invention bind to the liposomes at neutral pH, which is important since liposomes used in a patient will of course first be exposed to the almost neutral pH (7.4) of the bloodstream.

H. Liposome Contents

Therapeutic agents which may be used are any compounds, including the ones listed below, which can be stably entrapped in liposomes at a suitable loading factor and administered at a therapeutically effective dose (therapeutically effective doses are indicated below in parentheses after each compound; $m^2$ refers to body surface area, calculated by standard methods). These include amphipathic antitumor compounds such as the plant alkaloids vincristine (1.4 mg/ $m^2$), vinblastine (4–18 mg/ $m^2$) and etoposide (35–100 mg/ $m^2$), and the anthracycline antibiotics including doxorubicin (60–75 mg/ $m^2$), epirubicin (60–120 mg/ $m^2$) and daunorubicin (25–45 mg/ $m^2$). Water-soluble antimetabolites such as methotrexate (3 mg/ $m^2$), cytosine arabinoside (100 mg/ $m^2$) and fluorouracil (10–15 mg/kg), the antibiotics such as bleomycin (10–20 units/$m^2$, mitomycin (20 mg/$m^2$), plicamycin (25–30 $\mu$g/$m^2$) and dactinomycin (15 $\mu$g/$m^2$), and the alkylating agents, including cyclophosphamides and derivatives thereof (3–25 mg/kg), thiotepa (0.30–0.4 mg/kg) and BCNU (150–200 mg/$m^2$) are also useful in this context.

Other suitable drugs include aclacinomycin, idarubicin, mitoxantrone, cisplatin and other Platinum II analogs. The liposomes may also contain the taxanes including taxol, taxotere, dihydroxytaxanes, camptothecines and other taxane derivatives and isolates. In addition, the liposomes may contain encapsulated tumor-therapeutic peptides (e.g., plant or bacterially derived toxins) and protein drugs such as IL-2 and/or TNF, and/or immunomodulators, such as M-CSF, which are present alone or in combination with anti-tumor drugs, such as anthracycline antibiotic drugs. The liposomes may contain fluorinated pyramidine and purine bases or nucleosides.

The liposomes may also contain nucleic acids such as oligonucleotides containing natural or modified bases and having a phosphodiester internucleotide linkage or modified internucleotide linkages such as a phosphorothioate or polyamide linkages. This is a particularly advantageous use of liposomes, since the liposome membrane protects the nucleic acids from nucleases in the blood plasma. One of skill will recognize that nucleic acids may be used as antisense or triplex-forming molecules to block transcription and translation through binding of DNA or RNA. Alternatively, the nucleic acids may be used to transform cells and to induce the expression of heterologous proteins. In this latter context, the nucleic acid will comprise an expression cassette which includes the nucleic acid sequence encoding the protein to be expressed under the control of a promoter. Similarly, the nucleic acids may be, or may encode, ribozymes to target and cleave particular nucleic acid sequences within a cell.

Additional drugs which can be contained in liposomes of the invention are convential antibiotics such as ampicilin gentamycin, and cyclosporins, and antifungal agents such as amphotericin B, and less conventional drugs, such as ricin B chain or Pseudomonas exotoxin. Further, the liposomes can contain radioisotopes. For example, liposomes with targeting moieties such as antibodies or antibody fragments (such as Fab' fragments) or ligand for receptors overexpressed or preferentially expressed by a cell of interest (such as the folate receptor, which is overexpressed by some cancer cells) will preferentially bind to the targeted cells. Radioisotopes carried by the liposomes can be used as imaging agents, for example, to locate sites of tumor cells or to kill the cell targeted. The liposome can further contain a detectable label to permit detection of cells which take in the liposome or to which the liposome binds. Electronic transponders, fluorescent moieties, colorimetric labels, and numerous other labels known in the art may be used.

I. Loading Therapeutic Compositions into Liposomes

The methods of loading conventional drugs into liposomes are well known to those of skill in the art. The most common methods include an encapsulation technique and the transmembrane potential loading method. In the encapsulation technique, the drug is placed into the buffer from which the liposomes are made. The latter method has been described in detail in U.S. Pat. No. 4,885,172, U.S. Pat. No. 5,059,421, and U.S. Pat. No. 5,171,578, the contents of which are incorporated herein by reference.

Briefly, the transmembrane potential loading method can be used with essentially any conventional drug which can exist in a charged state when dissolved in an appropriate aqueous medium. Preferably, the drug will be relatively lipophilic so that it will partition into the liposome membranes. A transmembrane potential is created across the bilayers of the liposomes or targeting moiety liposome conjugates and the drug is loaded into the liposome by means of the transmembrane potential. The transmembrane potential is generated by creating a concentration gradient for one or more charged species (e.g., $Na^+$, $K^+$, and/or $H^+$) across the membranes. This concentration gradient is generated by producing liposomes or targeting moiety-liposome conjugates having different internal and external media. Thus, for a drug which is positively charged when ionized, a transmembrane potential is created across the membranes which has an inside potential which is negative relative to the outside potential, while for a drug which is negatively charged, the opposite orientation is used.

J. Liposome Clearance From the Blood and Assays Therefor

Liposome localization in a target tissue is enhanced if the liposome has an extended liposome lifetime in the bloodstream following administration. That is, a sufficient proportion of liposomes administered to a mammal, such as a patient in need thereof, must be both stable while circulating in the bloodstream (that is, the liposome should not release a high proportion of its contents), and not cleared from the circulation, to permit effective amounts of a therapeutic agent to reach the target tissue.

The RES, which consists of circulating macrophages, as well as the fixed macrophages of the liver (known as the Kupffer cells), spleen, and other organs, removes foreign particulate matter, including liposomes, from blood circulation. E.g., Saba, T., *Arch. Intern. Med.* 126:1031–1052 (1970). Multilamellar liposomes containing phosphatidylcholine and cholesterol as their principal lipid constituents have been shown to be removed from blood with a half life of 5–15 minutes following intravenous injection. See, e.g., Jonah et al., *Biochem. Biophys. Acta* 401:336–348 (1975); Juliano et al., *Biochem. Biophys. Res. Comm.* 63:651–658 (1975); Woodle, U.S. Pat. No. 5,013,556. In preferred embodiments of the invention, the liposomes have a clearance half life of about an hour or more, more preferably have a clearance half life of about 2 hours or more, and even more preferably have a clearance half life of about 4 hours or more. In more preferred embodiments, the liposomes have a clearance half life of about 8 hours or more, or even about 10 hours or more. In the most preferred embodiments, the liposomes are not cleared from the bloodstream by the RES for about 12 hours or more.

One measure of liposome lifetime in the bloodstream is the blood/RES ratio, determined at one or more selected times after liposome administration. Typically, liposomes containing a label (e.g. a fluorescent marker, an electron dense reagent, or a radioactive marker), either internal in the liposome or bound to a lipid comprising the liposome, are injected into a test organism. A fixed period of time later, the organism is sacrificed and the amount of label detected in the blood (e.g. by measuring luminescence, or by scintillation counting) is compared to that localized in particular tissues (e.g. liver or spleen).

The time course of retention of liposomes in the blood may also simply be determined by sampling blood from the subject at fixed intervals after administration to the subject of label-containing liposomes and determining the amount of label remaining in the subject's circulation. The result may be expressed as the fraction of the original dose. Assays for liposome clearance half life are also taught in, e.g. Woodle, U.S. Pat. No. 5,013,556, at columns 8–9 and at Example 5.

K. Assaying Uptake into the Cytoplasm of Target Cells and Determining Tissue Distribution Uptake and internalization of liposomes into the cytoplasm of target cells may similarly be determined by administering liposomes containing a label (e.g. fluorescent marker, electron dense reagent, or radioactive marker) and subsequently detecting the presence or absence of that label in the cytoplasm of the target cell. For example, a liposome containing a fluorescent marker, such as rhodamine conjugated to the lipid constituting the liposome itself, may be administered to the organism or simply to cells in culture. The tissues or cells may then be fixed and the fluorescence detected using fluorescence-microscopy. Similarly, an electron-dense label (e.g., gold) may be used and detected using electron microscopy. One of skill in the art will recognize that many labels are suitable and the method of detection will reflect the choice of label.

L. Pharmaceutical Compositions

Pharmaceutical compositions comprising liposomes of the invention are prepared according to standard techniques and further comprise a pharmaceutically acceptable carrier. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. These compositions may be sterilized by conventional, well known sterilization techniques.

The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, including, for example, sodium acetate, sodium lactate, sodium chloride, potassium chloride, and calcium chloride. Additionally, the liposome suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

The concentration of liposomes in the pharmaceutical formulations can vary widely, i.e., from less than about 0.05%, usually at or at least about 2–5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, liposomes composed of irritating lipids may be diluted to low concentrations to lessen inflammation at the site of administration. The amount of liposome administered will depend upon the liposome used, the disease state afflicting the patient, the therapeutic agent being delivered, and the judgement of the clinician. Generally the amount of liposomes administered will be sufficient to deliver a therapeutically effective dose of the particular pharmacological agent. The quantity of liposomes necessary to deliver a therapeutically effective dose can be determined by uptake assays as described above. Therapeutically effective dosages for various pharmacological agents are well known to those of skill in the art and representative ranges are given for a number of pharmaceuticals above. Typical liposome dosages will generally be between about 0.01 and about 50 mg per kilogram of body weight, and are preferably between about 0.1 and about 10 mg/kg of body weight.

Preferably, the pharmaceutical compositions are administered parenterally, i.e., intraarticularly, intravenously, intraperitoneally, subcutaneously, or intramuscularly. More preferably, the pharmaceutical compositions are administered intravenously or intraperitoneally by a bolus injection. Particular formulations which are suitable for this use are found in *Remington's Pharmaceutical Sciences,* Mack Publishing Company, Philadelphia, Pa., 17th ed. (1985) and 18$^{th}$ Ed. (1990). Typically, the formulations will comprise a solution of the liposomes suspended in an acceptable carrier, preferably an aqueous carrier. A variety of aqueous carriers may be used, e.g., water, buffered water, 0.9% isotonic saline, and the like. These compositions may be sterilized by conventional, well known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

EXAMPLES

The invention is illustrated by the following examples. These examples are offered to illustrate, but not to limit, the present invention.

Example 1.

This example demonstrates that copolymers can confer pH sensitivity to liposomes which are composed of intrinsically non-pH sensitive phospholipids.

Materials and Methods

Chemicals

NIPA, MAA and 2,2'-azobisisobutyronitrile (AIBN) were purchased from Eastman Kodak (Rochester, N.Y.). NIPA was purified before use, following the procedure described by Gehrke et al. (Gehrke, S. H. et al., *Polymer Int.* 29:29–36 (1992)). MAA was distilled at 55° C. and 73 cm Hg vacuum before use. AIBN was dissolved in ethanol, filtered, recrystalized in water and dried under vacuum. ODA was obtained from Aldrich (Milwaukee, Wis.) and used as received. EPC, cholesterol (Chol) and PEG-PE ($M_{r\ PEG}$=2000) were from Avanti Polar Lipids (Alabaster, Ala.). Fluorescent markers were obtained from Molecular Probes (Eugene, Oreg.).

Synthesis, Molecular Weight and Phase Transition Determine of Copolymers

NIPA, MAA, ODA (94:5:1 or 95:5:0 molar ratio) and AIBN (0.12% m/v) were dissolved in distilled 1,4-dioxane. The dioxane mass was 11 times the total monomer mass. The solution was degassed by bubbling $N_2$ for 15 min, heated to 65° C. and then maintained at that temperature for 15 h while being continuously stirred. Polymers were recovered by precipitation in diethylether, resolubilized in tetrahydrofuran, reprecipitated and extensively washed with diethylether. Polymers were then dried under vacuum for 5 days. The average molecular weights of polymers were determined by gel premeation chromatography as previously described (Merkly, A. et al., *J. Biomat. Sci. Polym. Ed.* 4:505–516 (1993)). Monodisperse polystyrene standards were used for calibration. The weight average molecular weights of poly(NIPA-co-MAA) and poly(NIPA-co-MAA-co-ODA) were 8730 and 9760, respectively. Phase transition pH of polymers was determined by 900 light scattering ($\lambda_{cm}$=450 nm) after 5 min incubation at 37° C. in MES buffered saline (100 mM MES, 2 mM EDTA, 144 mM NaCl) of pH values ranging from 4.7 to 6.3. Assuming that the initial molar ratio of each component is preserved after polymerization, the number of anchors per polymer chain (N) can be calculated using the following equation:

$$N=(M_{wPOLYMER} \cdot f_{ODA})/(M_{wNIPA} \cdot f_{NIPA}+M_{wMAA} \cdot f_{MAA}+M_{wODA} \cdot f_{ODA}) \quad (1)$$

where $M_{w\alpha}$ and $f_\alpha$ are the molecular weight and the molar fraction of comonomer $\alpha$ respectively, and $M_{wPOLYMER}$, the molecular weight of the copolymer.

Liposome Preparation, Characterization and Leakage Assay

Unilamellar liposomes (20 mM) composed of either EPC or EPC/Chol/PEG-PE (3:2:0.3 molar ratio) were prepared by the reverse-phase evaporation method (Szoka, F. C. *Proc. Natl. Acad. Sci. USA* 75:4194–4198 (1978)) followed by repeated extrusion through a 0.1 $\mu$m pore membrane (Szoka, F. C. et al., *Biochim. Biophys. Acta* 601:559$\mu$571 (1980)). Encapsulation of fluorescent markers into liposomes was performed by using an isotonic aqueous solution of HPTS-DPX-HEPES (35 mM-50 mM) pH 7.2. Untrapped dye was removed by gel exclusion chromatography on Sephadex G-50. Phospholipid concentrations were determined by phosphate assay (Morrison, W. R. *Anal. Biochem.* 7:281–284 (1964)). Liposomes were mixed with polymers and gently stirred overnight at 4° C. to form liposome-polymer complexes. The mean diameter of EPC liposomes and SSL were 160±40 un and 125±30 nm, respectively, as determined by dynamic light scattering (Coulter N4 Particle Size Analyzer) and remained unchanged by the presence of the polymer at the polymer/lipid ratios tested. Ten microliters of the complex (corresponding to 280 $\mu$g of lipid) were added to 2 mL of buffer and the release of liposome contents was monitored by fluorescence dequenching assay using liposomes with encapsulated HPTS-DPX. The extent of contents release was calculated from excitation fluorescence intensity of HPTS at $\lambda_{ex}$=413 nm after a 5 min exposure to different pH at 37° C. (pH-independent isosbestic point, $\lambda_{em}$=512 nm (Daleke, D. L. et al., *Biochim. Biophys. Acta* 1024:352–366 (1990)) over that obtained after sample lysis in 0.1% (m/v) $C_{12}E_8$ (100% release). Zeta potentials were derived from electrophoretic mobility measurements in 2 mM Tris-HCl, pH 8, containing 10% sucrose (m/v), using a Zetasizer 4 (Malvern Instruments, Ltd., UK) after adjustment to a negatively charged standard (AZ55, Malvern).

Results

FIG. 1 shows the effect of pH on the solubility of poly(NIPA-co-MAA) and poly(NIPA-co-MAA-co-ODA) in buffer. Both copolymers exhibit a discrete phase transition (cloud point) between pH 5.7 and 5.1 at 37° C. These polymers are soluble above pH 5.7 and start to precipitate as pH decreases, the phase transition being fully reversible. It should be noted that the pH range where the phase transition of these polymers occurs is similar to that of the endosomal/lysosomal compartments of the cell (Mellman, I. et al., *Ann. Rev. Biochem.* 55:663–700 (1986)). It has been shown that the incorporation of a small fraction of an ionizable comonomer in the structure of poly(NIPA) can lead to a LCST that becomes sensitive to pH (Taylor, L.D. et al. *D. J Polym. Sci.* 13:2551–2570 (1975); Chen, G. et al., *Nature* 373:49–52 (1995)). At neutral pH, the carboxylic groups of MAA are ionized and the LCST is shifted above 37° C. because of the higher overall hydrophilicity of the copolymer as compared to the homopolymer of NIPA. At acidic pH the protonation and removal of charge from MAA brings the LCST back to a value below 37° C., and induces the precipitation of the polymer, which is predominantly driven by the hydrophobic interactions between the isopropyl side groups of NIPA (Feil, H. et al., *Macromolecules* 26:2496–2500 (1993); Dong, L. C. et al., *J. Controlled Release* 15:141–152 (1991)). The presence of 1 mol % ODA, which was added to allow the anchoring of the polymer to the liposomes, does not change the phase transition pH of polyNPA-co-MAA). The hydrophobic substituent may not be exposed to water but rather forms a micellar structure protected from water by the poly(NIPA) chains, and therefore does not make a hydrophobic contribution to the phase transition (Winnik, F.M. et al., *Can. J. Chem.* 73:2030–2040 (1995) (hereafter, "Winnik 1995")).

Figure 2:
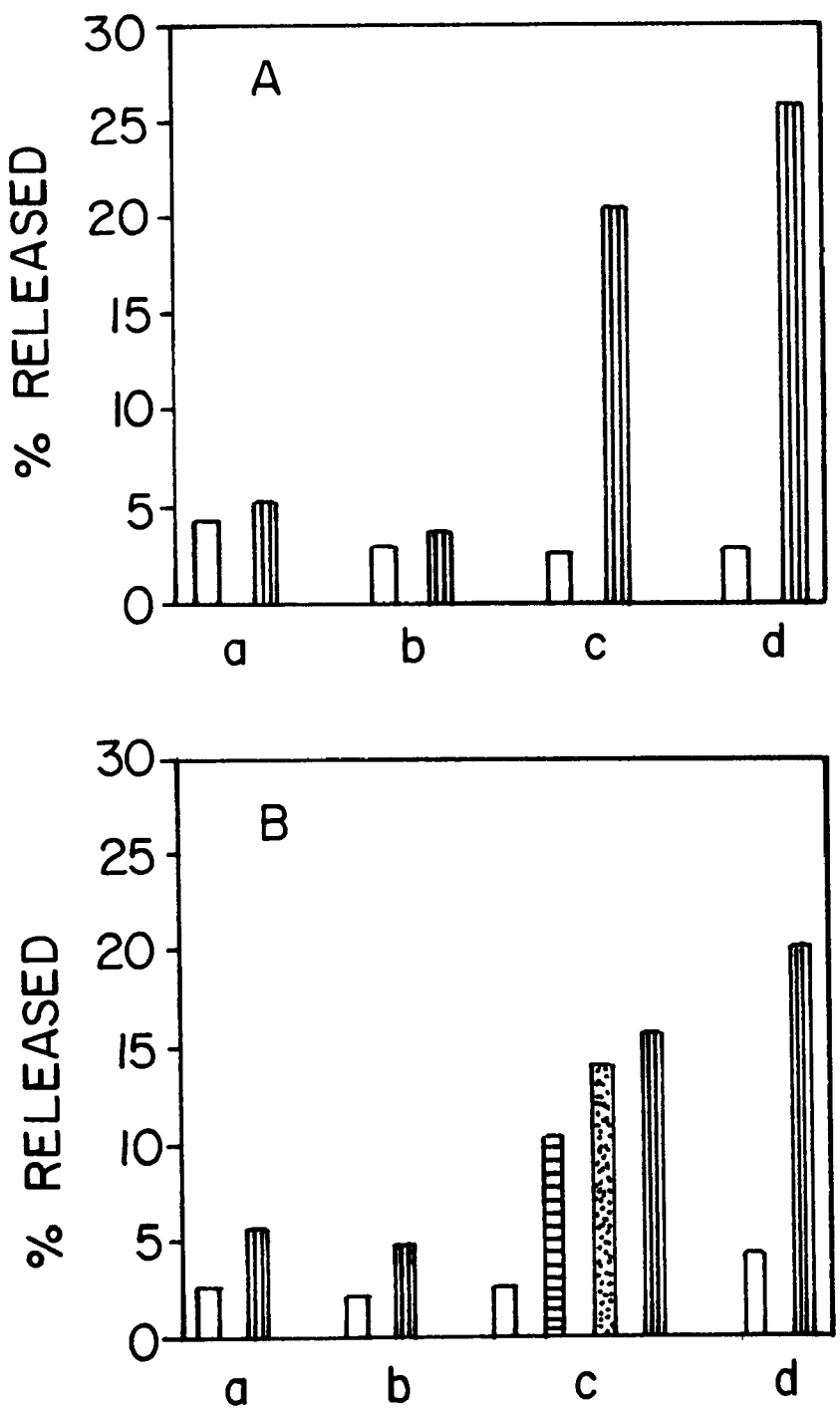
FIG. 2. Release of entrapped fluorescent marker after 5 min incubation at 37° C. from EPC liposomes (FIG. 2A) and sterically stabilized liposomes (FIG. 2B). or each graph, the columns are as follows: (a) control liposomes; (b) liposomes in the presence of poly(NIPA-co-MAA), polymer/lipid=0.28 (m/m); (c) liposomes in the presence of poly(NIPA-co-MAA-co-ODA), polymer/lipid=0.28 (m/m); (d) liposomes in the presence of poly(NIPA-co-MAA-co-ODA), polymer/lipid-0.56 (m/m). Open bars, pH 7.2; closed bars, pH 4.9; dashed bar, pH 5.3; dotted bar, pH 5.5. Values for duplicate varied than less than 8%.

The pH-triggered release of fluorescent markers from liposomes and liposome-polymer systems after a 5 min incubation at 37° C. is presented in FIG. 2. The decrease in pH from 7.2 to 4.9 produces a 10-fold increase in the total amount of dye released from EPC liposomes associated with poly(NIPA-co-MAA-co-ODA) (FIG. 2A, c and d). Interestingly, preincubation of liposomes with the same polymer lacking the alkyl chain does not induce pH-triggered liposomal leakage (FIG. 2A b). This indicates that the presence of alkyl chains in the structure of the copolymer is important for liposome pH-dependent response, possibly due to efficient complexation of the polymer to the liposome membrane via octadecyl chains, as previously shown for similar systems (Kim, J.C. et al., *J. Biochem.* 121:15–19 (1997); Winnik 1995). Acidic-mediated liposome leakage was only slightly enhanced (about 15%) by increasing the ODA-containing polymer to lipid mass ratio by a factor of two (FIG. 2A, c and d), suggesting a binding saturation process of the polymer to the liposome surface.

After addition of the alkyl chain grafted polymer to EPC liposomes, the samples remained transparent, whereas increased turbidity of liposome suspensions without polymer occurred in time over a period of few weeks at 4° C., presumably due to liposome aggregation (not shown). This phenomenon of stabilization over time was not observed upon addition of the copolymer lacking alkyl chains. Moreover, it has been reported that liposomes coated with copolymers of NIPA show reduced liposome interaction with plasma proteins including opsonins (Winnik 1995). These findings are consistent with a possible liposome stabilizing effect of such polymers. Stability in plasma and pharmacokinetics of polyNPA-co-MAA-co-ODA)-liposome complexes are currently under investigation in our laboratory.

SSL containing specific ligands at their surface are efficiently internalized by target tumor cells whereas SSL lacking the targeting device are not (Park, J. W. et al., *Proc. Natl. Acad. Sci. USA* 92:1327–1331 (1995); Kirpotin, D. et al., *Biochemistry* 36:66–75 (1997)). Therefore, it appears attractive to confer additional pH-sensitive properties to internalizable SSL formulations for tissue-specific intracytoplasmic drug delivery in vivo. Experiments on contents release with SSL show results similar to those obtained with EPC liposomes (FIG. 2B). The presence of cholesterol, and more importantly, the incorporation of 6 mol % PEG-PE, do not seem to prevent contents release upon acidification and in the presence of poly(NIPA-co-MAA-co-ODA). This is supported by electrophoretic mobility data showing that the zeta potential of liposome-poly(NIPA-coMAA-co-ODA) complexes (polymer/lipid=0.28 m/m, 0.02 mol/mol) are about −15 mV for EPC and −6 mV for SSL-associated polymer, respectively, whereas EPC and PEGylated liposomes show a neutral particle surface. This difference in zeta potential can be explained either by shielding of the polymer charge by PEG at the surface of the complex (Woodle, M. C. et al., *Biophys. J.* 61:902–910 (1992)), or by reduced binding efficiency of polymer to PEG-coated liposomes.

Figure 3:
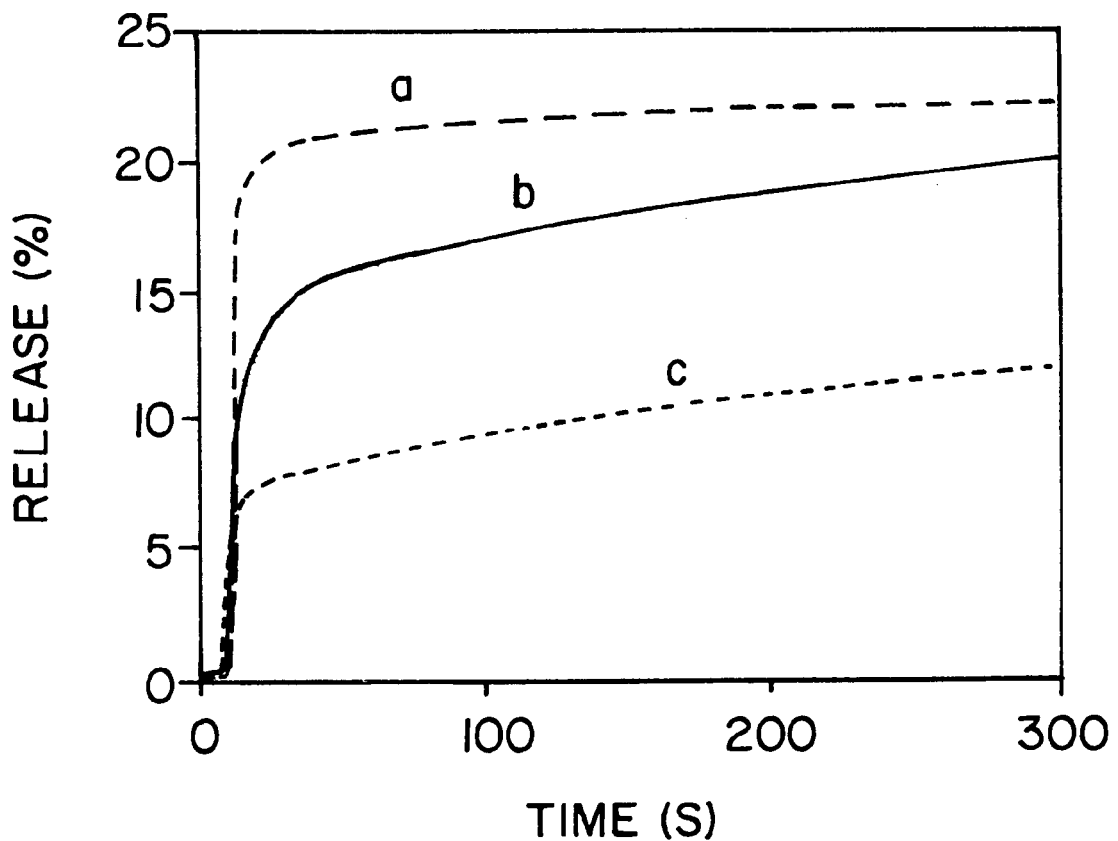
FIG. 3. Release kinetics of fluorescent marker from liposomes at 37° C. in the presence of poly(NIPA-co-MAA-co-ODA) with polymer/lipid=0.28 (m/m). The lines represent the results for the following liposomes, under the following pH conditions: (a) EPC-polymer at pH 4.9 (b) SSL-polymer at pH 4.9, (c) SSL-polymer at pH 5.5.

The release of HPTS from SSL after 5 min at low pH is about 15% lower than for EPC liposomes in the presence of poly(NIPA-co-MAA-co-ODA) at both polymer to lipid ratios tested (FIG. 2). The release kinetics of HPTS from EPC and PEGylated liposomes complexed to poly(NIPA-co-MAA-co-ODA) show that 15–20% of the liposome contents are released within 30–40 seconds irrespective of the liposome lipid composition (FIG. 3). After 5 min of treatment at acidic pH (4.9), EPC-complexes have reached their plateau for contents leakage, whereas SSL-complexes have not (FIG. 3, compare lines a and b). It seems that the stabilizing effect of PEG-PE (or the presence of cholesterol or both) slows down the release of fluorescent markers from liposomes. Furthermore, contents release from SSL increases with decreasing pH within the transition pH range of the polymer (FIG. 2B c, and FIG. 3b and c). Importantly, liposome destabilization starts at pH values corresponding to those of endosomes.

Incubation time of SSL with poly(NPA-co-MAA-co-ODA) is an important parameter influencing the efficiency of the polymer to confer pH-sensitivity on SSL. Indeed, the addition of SSL and polymer to the acidic medium without prior incubation did not show significant acid-mediated release of HPTS (5;8%). Premixing of SSL with this copolymer for 90 seconds, however, led to release of 10% of the contents (a 72% improvement), which in turn is about half that obtained after an overnight incubation of SSL with the copolymer at 4° C.

pH-triggered release of contents from liposomes by poly (NIPA-co-MAA-co-ODA) may result from a transient destabilization of the liposome membrane due to the conformational change of the polymer upon acidification. Moreover, charge neutralization by protonation of the polymer carboxyl groups renders the polymer more hydrophobic and more likely to interact strongly with the lipid bilayer, causing membrane structure defects. A possible partial withdrawal of the anchor groups from the lipid bilayer upon contraction of the polymer (Polozova, A. et al., *Biochim. Biophys. Acta* 1326:213–224 (1997) may also be involved.

Several hypotheses have been formulated to explain why only a fraction of the liposome contents (20–25%) were released. Perturbation of the lipid membrane could be temporary, as lipid molecules quickly rearrange themselves after the collapse of the polymer, stopping further liposome leakage. There also may be only some liposome populations containing sufficient amounts of polymers to induce release of fluorescent markers. A tendency of hydrophobically-modified copolymers of NIPA to form polymer-rich domains and phase separation of the contracted polymer at the liposome surface have been reported by others (Simon, J. et al., Chem. Phys. Lip. 76:241–258 (1995)), suggesting that events such as pore-like formation can also be involved in the mechanism of release.

Membrane-anchored ionic polymers have previously been employed to induce liposome destabilization and/or fusion but showed disadvantageous requirements such as very large polymer concentration (Tirell, D.A. et al., Ann. N. Y. Acad. Sci. 446:237–248 (1985)) or very high charge density of the polymers, or both (Tirell, D. A. et al., supra; Kono, K. et al., Biochim. Biophys. Acta 1193:1–9 (1994)) to obtain the desired effect. Moreover, it has been shown that the pH-sensitivity of PE-based liposome formulations decreases with increasing amount of either cholesterol (Liu, D. et al., Biochim. Biophys. Acta 981:254–260 (1989)) or PEG-PE (Slepushkin, V. A. et al., J. Biol. Chem. 272:2382–2388 (1997)).

Our studies indicate that poly(NIPA-co-MAA-co-ODA) confers pH-sensitivity to SSLs containing up to 40 mol % cholesterol and 6 mol % PEG-PE. This is a fairly high percentage of PEG-PE, and is considered to permit a good circulation time in the blood. Surface charged liposomes can be potentially rendered pH-responsive by such copolymers, however, electrostatic repulsion between poly(NIPA-co-MAA-co-ODA) and negatively charged liposomes can alter their association efficiency. For cationic (positively charged) liposomes, which are only used where the positive charge of the liposome has some particular advantage, the NIPA or other anionic (negatively charged) copolymer should be added in amounts which retain the overall positive charge of the liposome.

Since the number of anchors per polymeric chain was determined to be less than one (N=0.86, see Eq. 1 in Materials and Methods), one can expect an improved pH-mediated release of liposomal contents if N is increased. This promising pH-sensitive system will permit more efficient intracytoplasmic drug delivery in vivo.

Example 2.

This Example shows that changing the composition of the copolymer permits modulation of the pH at which liposomal contents are released.

Material and Methods

The copolymer and liposome preparation, the determination of phase transition pH and the release studies were performed as previously described in Example 1. The copolymers contained NIPA, 5% MAA, and 1, 2 or 4% ODA respectively. In order to evaluate the actual binding of the copolymer on liposomes, a fluorescent copolymer was synthesized by introducing 0.3 mol 1-pyreneacrylic acid during polymerization. 1-pyreneacrylic acid is obtained from 1-pyrenecarboxylaldehyde and malonic acid and is crystalized from ethyl malonate (Bergmann and Bograchov, J. Am. Ch. Soc. 62:3016–3018 (1940). The separation between the bound and the free copolymer was obtained on a Sepharose 2B column (interior diameter 1 cm, 23 cm) The binding of copolymer on liposomes was determined by fluorescence measurements using pyrene-labeled copolymer. Except as otherwise specified the binding of the polymer on the liposomes was determined after 16 h incubation at 4° C.

Results

The fluorescent copolymer showed the same phase transition pH, which was between pH 5 and 6. By adding an increasing concentration of copolymer, the liposome surface was progressively saturated by the copolymer. The maximal binding of the copolymer to EPC liposomes was 0.04 µg/µg bound copolymer/lipid ratio. Comparing the binding of the copolymer to liposomes of various lipid compositions after 16 h incubation, the presence of cholesterol (CHOL) had no influence on the copolymer binding capacity. The presence, however, of polyethyleneglycol (PEG) on the surface of the liposomes almost totally inhibited the fixation of a high molecular weight (34 kDa) copolymer containing 2% ODA. To overcome this interaction, the copolymer was added to stealth liposomes during the preparation procedure (the procedure employed was reverse phase evaporation). This resulted in significant binding of copolymer even in presence of PEG.

Previous studies showed that in the absence of copolymer, or in the absence of an anchor (ODA), liposomes did not display a tendency to release HPTS at acidic pH. Increasing the content of ODA content in the copolymer resulted in an increase in HPTS release. The release studies at various pH showed that in the presence of copolymer, liposomes loaded with HPTS released a significant proportion of HPTS between pH 5.5 and 4.9. This increasing release can be directly correlated to the phase transition pH of the studied copolymer.

The release of HPTS from liposomes of various lipid compositions was compared. The results showed that the liposomes did not release the tracer at physiological pH, whereas liposomes incubated with 2% ODA released a significant proportion of encapsulated tracer (up to 70%, in the case of EPC liposomes) at pH 4.9. The presence of CHOL only slightly modified the release of the tracer. This result can be related to the similar binding amount previously observed between liposomes containing CHOL or not. The results also suggested that higher molecular weight polymers intefered with binding to the liposome during incubation procedures. Thus, if incubation of the polymer with the liposomes is contemplated for associating the polymer with the liposomes, it is preferred that the polymer have a molecular weight below 30 kD, more preferably should be below 25 kD, and even more preferably, should be below 20 kD. If a polymer with a larger molecular weight is used, the percentage of the alkyl group or other hydrophobic polymer (anchor) should be increased slightly for each additional 2 kD of molecular weight to compensate for the consequent reduced binding efficiency.

As noted, the copolymer can be incubated with the liposomes. Improved HPTS release from Stealth® liposomes has been observed, however, when the copolymer (2% ODA) was incorporated during the liposome preparation procedure. Liposomes incubated with copolymer containing 4% ODA released HPTS to a similar extent. Thus, incorporation of the polymer during liposome preparation resulted in the same release of contents as did that seen in liposomes incubated with twice the proportion of ODA as an anchor. Release studies have been also performed after free copolymer separation on column. The results have shown that there is a slight desorption of the copolymer incubated with liposomes, whereas no difference is observed in the release capacity, when the polymer is incorporated during liposome preparation.

The incubation of solid liposomes (DSPC/CHOL 3:2) with a 2% ODA copolymer markedly increased the release of HPTS at pH 4.9 compared to a 1% ODA copolymer. Thus, the polymers described herein can confer pH sensitivity even upon liposomes with a high phase transition temperature, which are rigid and "solid" at typical physiological temperatures (such as 37° C.). Fluid liposomes (which have a phase transition temperature not far from typical physiological temperatures, and are accordingly considered fluid rather than rigid) of POPC/CHOL 3:2 are similar to EPC/CHOL ones and show a comparable release of HPTS.

These studies show that separation of bound and free copolymer can be obtained on Sepharose columns, that there is an effective binding of the copolymer on liposomes, that the percentage of the contents of the liposomes released can be increased by either increasing the amount of anchor in the copolymer or by incorporating the copolymer during liposome preparation, and that liposomes presenting a high phase transition (above 37° C.) can be rendered pH-responsive after incubation with the copolymer.

Example 3

This Example shows the determination of the pH-sensitivity of different liposome compositions in the presence of a polymer containing 2 mol % ODA and, the elucidation of the mechanism by which these polymers destabilize liposomal membranes. It further shows that liposomes were targeted to KB-31 nasopharyngeal epidermoid carcinoma cells using folate covalently attached to a PEG-DSPE anchor and the effect of the polymer on both uptake by KB-31 cells and that the cytotoxicity of encapsulated doxorubicin was determined. Many tumors overexpress folate receptors on their surface due to their high metabolic rate. Binding of the folate to the folate receptor resulted in endocytosis of the liposome and thus the exposure of the liposome to the low pH-environment found in the endosome.

Methods

Liposomes were prepared by a combination of six cycles of rapid freeze-thaw, alternatively placing the lipid suspension in dry ice/ethanol and then a 60° C. water bath, and then extrusion through 100 nm and 50 nm filters. HPTS was encapsulated in liposomes by including it and DPX (a water soluble fluorescence quencher) at concentrations of 35 mM HPTS and 50 mM DPX in the hydrating solution (pH 8.0). Doxorubicin was encapsulated in liposomes using an ammonium sulfate remote-loading technique as described previously (Haran et al., Biochim. Biophys. Acta 151:201–215 (1993); Lasic et al., FEBS Lett. 312:255–258 (1992)). Briefly, liposomes were hydrated in 250 mM ammonium sulfate (pH 5.5) and extruded through 100 and 50 nm filters. The extruded liposomes were then separated from unencapsulated ammonium sulfate on a Sephadex G-75 size-exclusion column and collected in a 15 ml cell culture tube containing the dry drug. Doxorubicin was added at a concentration of 1.5 mg of doxorubicin (9 mg of total powder since it also contains lactose monohydrate at a ratio of 1:6 w/w). After briefly vortexing to make sure all the drug was in solution, the liposomes were incubated for 1 h at 55° C. in a hot water bath to finish the loading process. The liposomes were then separated from any free doxorubicin on a size-exclusion column.

The liposomes prepared with doxorubicin were composed of HSPC:Chol:PEG-DSPE (3:2:0.045) or HSPC:Chol:folatePEG-DSPE (3:2:0.03). The folate-PEG-DSPE was incorporated at a slightly higher mol % than that used in the references cited above due to the elevated molecular weight of the polymer used (3450 g/mol compared to 2000 for PEG-DSPE). Phospholipid was determined using a modification of the Bartlett assay (Bartlett, J. Biol. Chem., 234:466–468 (1959)) and doxorubicin was determined by measuring the $OD_{485}$ of the liposome upon solubilizing in acid isopropanol (2N HCl: 2-propanol: $ddH_2O$ 3:7:90:6.3 v/v/v) and comparing it to a standard curve of free doxorubicin. The size of the liposomes was determined by photon correlation spectroscopy using a Nicomp particle size analyzer with volume weighting. The polymer was added to the drug-loaded liposomes at a polymer:lipid of 0.3 (w/w) and incubated at 37° C. overnight. The liposomes were then passed over a Sepharose 4B size-exclusion column to remove any unbound polymer and to detect any leakage of doxorubicin caused by incorporation of the polymer.

For lipid mixing experiments, liposomes comprised of EggPC:Chol:N-NBD-PE:N-Rh-PE (3:2:0.05:0.05) were mixed with unlabeled liposomes comprised of EggPC:Chol (3:2) in a 1:10 molar ratio. All liposomes had polymer incorporated into their outer monolayer by an overnight incubation at 4° C. (polymer:lipid ratio of 0.3 w/w). The lower temperature was used with these liposomes as compared to the 37° C. used for HSPC:Chol liposomes due to the lower phase transition of the PC component. The mixed liposomes were injected into low pH buffers and fluorescence ($\lambda ex=470 \lambda cm=520$). was measured continuously over time. A 100% control liposome formulation of EggPC:Chol:N-NBD-PE:N-Rh-PE (3:2:0.005:0.005) was prepared and used as the standard for 100% lipid mixing. Light scattering was also determined simultaneously as a measure of the degree of liposome aggregation. Fluorescence energy transfer experiments with N-NBA-PE and N-Rh-PE demonstrate lipid mixing, which is necessary for membrane fusion, by measuring the increase in NBD fluorescence upon dilution of the lipid probes in unlabeled membranes and thus reducing the amount of fluorescence-energy transfer from NBD to Rhodamine (Struck et al., Biochemistry 20:4093–4099 (1981)).

Results

Characterization of the Liposomes

Drug-to-lipid ratios were determined both before and after polymer addition to see if adding the polymer resulted in any destabilization of the liposomes. Following addition of the polymer, liposomes lost approximately 5% of their total doxorubicin, indicating only a minor disruption of the liposome resulted from polymer introduction. The size of the liposomes was similar—73.9 vs 83.7—for the two preparations. The folate-PEG-DSPF, containing composition is likely closer to the 74 nm shown for the non-targeted liposomes, but was weighted slightly higher due to a small amount of contamination with larger particles. This size is well within the optimal size range for liposome use in vivo. Liposomes are taken up by macrophages of the RES in a fashion dependent on the size of the liposomes; smaller liposomes are taken up less readily than large liposomes.

pH-Dependence of Doxorubicin Leakage from Folate-PEG-DSPE:HSPC:Chol and PEG-DSPE:DSPC:Chol Liposomes Following injection of liposomes into buffers of varying pH, doxorubicin leakage was measure as an increase in doxorubicin fluorescence following a relief of self-quenching. Experiments were completed either in the absence or presence of 1 mM CaCl$_2$. Calcium is found in human plasma at a total concentration of 2.5 mM and a free concentration of approximately 1.1 mM. Additionally, calcium has been shown previously to destabilize other pH-sensitive liposome formulations in a manner which is synergistic with the effect on pH (Düzgünes et al. *Biochemistry* 24:3091–3098 (1985); Ellens et al. *Biochemistry* 24:3099–3106 (1985); Collins et al., *Chem. Phys. Lipids* 55:339–349 (1990)). While polymers likely destabilize membranes by a different mechanism, the dehydrating capability of calcium is an important consideration in membrane stability studies.

PEG-DSPE:HSPC:Chol liposomes either with or without the incorporated copolymer were incubated at pH 4.5 and doxorubicin fluorescence was measured continuously. While fluorescence values showed values of approximately 70% for the liposomes incubated in the presence of polymer, those incubated in the absence of polymer had less than 10% leakage. In addition, the low level of fluorescence seen in the absence of polymer was most likely residual fluorescence from unquenched doxorubicin and not leakage. Doxil®, which is also a liposomal doxorubicin formulation, leaks doxorubicin very slowly at neutral pH. Thus, these are very stable liposomes. Leakage of these liposomes at low pH values has not previously been extensively studied. In studies conducted on liposomes of formulations similar to those of Doxil®, the liposomes showed a minimal release of their contents at low pH, and were therefore found to be pH insensitive. Identical liposomes coated with copolymers of the invention showed pH sensitivity, with the extent of leakage increasing as the pH decreased.

The effect of the presence of Ca$^{2+}$ on doxorubicin leakage was also investigated. At pH 4.5, doxorubicin leakage was markedly increased at 1 mM CaCl$_2$, compared to leakage at the same pH, but in the absence of Ca$^{2+}$. Thus, under physiologically relevant conditions, stable doxorubicin-loaded liposomes rapidly leaked their contents when the pH was lowered to values observed in late endosomes or lysosomes (Anderson and Orci, *J. Cell Biol.* 106:539–543 (1988); Schmid et al., *Cell* 52:73–83 (1988)).

Studies on the Mechanism of Drug Release

Most pH-sensitive liposome formulations leak their contents due to a process known as "leaky" fusion, characterized by an initial dehydration of membrane surfaces and aggregation, resulting in a mixing of the membrane lipid components and leakage of encapsulated molecules. In the studies reported here, aggregation was not observed to result in doxorubicin leakage. To further clarify if fusion was responsible for leakage of these liposomes, it was decided to examine the pH-induced effect on the liposomes bearing the polymers using a lipid mixing assay. If these liposomes were similar to other membranes that undergo fusion, a large increase in the mixing of the lipid components would be expected. Aggregation was also observed by monitoring light scattering in the opposite detector in a florimeter set up in a T-configuration. This was compared to another liposome formulation previously shown to fuse under conditions of low pH in the presence of Ca$^{2+}$.

N-citraconyl-dioleoylphosphatidylethanolamine (cit-DOPE):DOPE liposomes have been previously shown to fuse and release water soluble contents markers (HPTS and calcein) in response to decreases in pH and increases in Ca$^{2+}$ concentrations in the incubation media. In the presence of 4 mM Ca$^{2+}$, an increase in lipid mixing for this formulation was seen both at pH 4.5 and at pH 5.5.

Aggregation is considered the first step of the fusion process, since membranes must come together before mixing of their lipid components can occur. When aggregation (as measured by light scattering) was measured simultaneously with lipid mixing, aggregation was shown to increase at a rate similar to that observed in the lipid mixing experiments.

The liposomes used for incorporation of the copolymer contain high concentrations of phosphatidylcholine and cholesterol, a combination usually refractory towards fusion. As described above, significant drug leakage did occur upon addition of the polymer. Lipid mixing experiments with these liposomes at pH 4.5, a condition at which significant drug leakage had been previously demonstrated, showed no lipid mixing. Additionally, when light scattering was measured, no increase in light scattering was observed. These two results indicate that fusion is not the mechanism resulting in drug release. The fact that fusion refractory lipids such as PC can be used with this copolymer are very exciting, since PC and cholesterol, and especially high phase transition phospholipids are usually required for maintaining stable drug formulations in the circulation.

Accumulation in KB-31 Cells

Doxorubicin uptake into KB-31 cells was measured as function of time to determine whether the polymer inhibits recognition of the targeting ligand by receptors on the cancer cells. Experiments completed previously with either folate or Fab' targeting molecules attached directly to the membrane interface demonstrated inhibition of endocytosis when PEG$_{2000}$-DSPE was incorporated into the membrane (Park et al., *Proc. Natl. Acad. Sci.* (USA) 92:1327–1331 (1995); Lee and Low, *J. Biol. Chem.* 269:3198–3204 (1994); Lee and Low, *Biochim. Biophys. Acta* 1233:134–144 (1995)).

The results reported herein were to the contrary. For these experiments, four different doxorubicin-loaded liposomes (+folate/+copolymer, +folate/−copolymer, −folate/+copolymer, −folate/−copolymer) were incubated with KB-31 cells and the amount of cell-associated doxorubicin was determined after specified times by measuring its fluorescence. The doxorubicin accumulation in KB-31 cells from liposomes targeted with folate and containing a polymer containing 2 mol % ODA was dramatically higher at each time point examined. It appears that at least some of the folate was recognized by the folate receptor and that the association of the targeted liposome was not reduced by addition of the anchored polymer. The difference between this and the results seen by Low and Park may have to do with the spacing of the anchors in the copolymer and thus the conformation of the polymer on the liposome surface. The polymer used in the studies reported here may pull the polymer closer to the surface of the liposomal membrane than did the polymers of Low and Park, affording better access of the folate to the folate receptor on the target cells.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A pH-sensitive, serum-stable liposome loaded with an agent and having a lipid bilayer, complexed with a molecule comprising
   (a) a thermally-sensitive polymer showing lower critical solution temperature behavior in aqueous solutions,
   (b) a hydrophobic substituent of less than 10 kD covalently bound to said thermally-sensitive polymer, and
   (c) a pH sensitive substituent covalently bound to said thermally-sensitive polymer, which pH sensitive substituent remains ionizable following said covalent bonding to said thermally-sensitive polymer, and whose pH sensitivity does not depend on cleavage of the covalent bond to said thermally-sensitive polymer, wherein said liposome and said molecule are complexed by the insertion of said hydrophobic substituent into the lipid bilayer of the liposome, and further wherein the liposome, when complexed to said molecule and in an aqueous solution, releases at least 20% of the agent when the pH of the solution is changed from pH 7.4 to pH 3.5.

2. The liposome of claim 1, wherein said thermally-sensitive polymer or copolymer is selected from the group consisting of: N-isopropylacrylamide, ("NIPA") poly (N-substituted acrylamides, poly(N-acryloyl pyyrolidine), poly(N-acryloyl piperidine, a poly(acryl-L-amino acid amide), a poly(vinyl alcohol) derivative, poly(ethyl oxazoline), hydroxypropyl acrylate, hydroxypropyl cellulose, hydroxyethyl cellulose,.polyvinyl acetate phthalate, hydroxypropyl methylcellulose acetate succinate, methylcellulose, hydroxymethyl cellulose, and cellulose.

3. The liposome of claim 1, wherein said thermally-sensitive polymer or copolymer comprises N-isopropylacrylamide ("NIPA").

4. A pH-sensitive, serum-stable liposome of claim 1, wherein said hydrophobic substituent is selected from the group consisting of an alkyl moiety and a hydrophobic polymer.

5. A method of conferring pH-sensitivity on, or increasing pH sensitivity of, a liposome loaded with an agent and having a lipid bilayer, said method comprising the step of complexing said liposome with a molecule comprising
   (a) a thermally-sensitive polymer showing lower critical solution temperature behavior in aqueous solutions,
   (b) a hydrophobic substituent of less than 10 kD covalently bound to said thermally-sensitive polymer, and
   (c) a pH sensitive substituent covalently bound to said thermally-sensitive polymer, which pH sensitive substituent remains ionizable following said covalent bonding to said thermally-sensitive polymer, and whose pH sensitivity does not depend on cleavage of the covalent bond to said thermally-sensitive polymer, 6. The liposome of claim 4 wherein said alkyl moiety comprises octadecyl acrylate ("ODA").

7. The liposome of claim 4 wherein said alkyl moiety comprises a double alkyl chain lipid.

8. The liposome of claim 7, wherein said double alkyl chain lipid is phosphatidylethanolamine.

9. The liposome of claim 1, wherein said pH sensitive (ionizable) moiety is an alkylacrylic acid.

10. The liposome of claim 9, wherein said alkylacrylic acid is selected from the group consisting of: methylacrylic acid, ethylacrylic acid, propylacrylic acid, and butylacrylic acid.

11. The liposome of claim 9 wherein said alkylacrylic acid is present at a mol % of the polymer or copolymer of between about 0.5% and about 10%.

12. The liposome of claim 1, wherein said liposome further comprises: polyethyleneglycol or a ganglioside.

13. The liposome of claim 1, wherein the clearance half life of the liposome is at least about 1 hour.

14. The liposome of claim 1, wherein the clearance half life of the liposome is at least about 4 hours.

15. The liposome of claim 1, wherein the clearance half life of the liposome is at least about 12 hours.

16. The liposome of claim 1, wherein said liposome comprises: molecules selected from the group consisting of: 1.2-distearoyl-sn-glycero-phosphatidylcholine-1,1,2,2-d4 ("DSPC"), 1-palmitoyl-2-oleoyl-sn-glycero-3-phosphatidylcholine ("POPC"), hydrogenated soy phosphatidylcholine ("HSPC"), egg phosphatidylcholine (EPC), and EPC/cholesterol/poly(ethylene glycol)-phosphatidylethanolamine "EPC/Chol/PEG-PE").

17. The liposome of claim 16, wherein the thermally-sensitive polymer is N-isopropylacrylamide ("NIPA"), the alkyl moiety is octadecyl acrylate ("ODA"), and the pH sensitive moiety is methacrylic acid ("MAA").

18. The liposome of claim 17 wherein said NIPA, MA,and ODA are in a molar ratio of about 94:5: 1, about 93:5:2, or about 91:5:4.

19. The liposome of claim 16 wherein said liposome comprises: EPC/Chol/PEG-PE in a molar ratio of about 3:2:0.3.

20. The liposome of claim 16, wherein said liposome comprises HSPC:Chol:PEG-1.2-distearoyl-sn-glycero-3-phosphatidylethanolamine ("DSPE").

21. The liposome of claim 1, wherein said liposome contains an agent selected from the group consisting of a drug, a radioisotope, a detectable label, a nucleic acid, a vector, and a ribozyme.

22. A method of delivering an agent to a cell said method comprising contacting said cell with a liposome of any of claims 1 through 9 or of claims 11 through 20.

23. The method of claim 22, wherein said contacting is caused by systemic administration of said liposome.

24. The method of claim 23, wherein said systemic administration is by injection or intravenous administration.

25. A method of claim, wherein said hydrophobic substituent is selected from the group consisting of an alkyl moiety and a hydrophobic polymer.

26. The method of claim 25, wherein said thermally-sensitive polymer is selected from the group consisting of: n-isopropylacrylamide ("NIPA"), poly (N-substituted acrylamides, poly(N-acryloyl pyyrolidine), poly(N-acryloyl piperidine, a poly(acryl-L-amino acid amide), a poly(vinyl alcohol) derivative, poly(ethyl oxazoline), hydroxypropyl acrylate, hydroxypropyl cellulose, hydroxyethyl cellulose, polyvinyl acetate phthalate, hydroxypropyl methylcellulose acetate succinate, methylcellulose, hydroxymethyl cellulose, and cellulose.

27. The method of claim 25, wherein said thermally-sensitive polymer comprises N-isopropylacrylamide ("NIPA").

28. The method of claim 25, wherein said alkyl moiety comprises octadecyl acrylate ("ODA").

29. The method of claim 25, wherein said liposome further comprises polyethyleneglycol.

30. The method of claim 25, wherein said liposome contains an agent selected from the group consisting of a drug, a radioisotope, a detectable label, a nucleic acid, a vector, and a ribozyme.

31. The method of claim 25, wherein said liposome comprises molecules selected from the group consisting of: 1,2-distearoyl-sn-glycero-phosphatidylcholine-1,1.2.2-d4 ("DSPC"), 1-palmitoyl-2-oleoyl-sn-glycero-3-phosphatidylcholine ("POPC"), hydrogenated soy phosphatidylcholine ("HSPC"). egg phosphatidylcholine (EPC). and EPC/cholesterol/poly(ethylene glycol)-phosphatidylethanolamine "EPC/Chol/PEG-PE").

32. The method of claim 25, wherein the thermally-sensitive polymer is N-isopropylacrylamide ("NIPA"), the alkyl moiety is octadecyl acrylate ("ODA"), and the pH sensitive moiety is methacrylic acid ("MAA"), and the NIPA, MAA, and ODA are present in a molar ratio of about 94:5:1, about 93:5:2, or about 91:5:4.

33. The method of claim 25, wherein said liposome comprises: egg phosphatidylcholine ("EPC"). cholesterol ("Chol") and poly(ethylene glycol)-phosphatidylethanolamine ("PEG-PE") ("EPC/Chol/PEG-PE")in a molar ratio of about 3:2:0.3.

* * * * *